United States Patent
Hyde et al.

(10) Patent No.: US 8,215,835 B2
(45) Date of Patent: Jul. 10, 2012

(54) TEMPERATURE-STABILIZED MEDICINAL STORAGE SYSTEMS

(75) Inventors: Roderick A. Hyde, Redmond, WA (US); Edward K. Y. Jung, Bellevue, WA (US); Nathan P. Myhrvold, Medina, WA (US); Clarence T. Tegreene, Bellevue, WA (US); William Gates, Redmond, WA (US); Charles Whitmer, North Bend, WA (US); Lowell L. Wood, Jr., Bellevue, WA (US)

(73) Assignee: Tokitae LLC, Bellevue, WA (US)

( * ) Notice: Subject to any disclaimer, the term of this patent is extended or adjusted under 35 U.S.C. 154(b) by 876 days.

(21) Appl. No.: 12/077,322

(22) Filed: Mar. 17, 2008

(65) Prior Publication Data
US 2009/0145793 A1 Jun. 11, 2009

Related U.S. Application Data

(63) Continuation-in-part of application No. 12/001,757, filed on Dec. 11, 2007, and a continuation-in-part of application No. 12/006,088, filed on Dec. 27, 2007, and a continuation-in-part of application No. 12/006,089, filed on Dec. 27, 2007, and a continuation-in-part of application No. 12/008,695, filed on Jan. 10, 2008, and a continuation-in-part of application No. 12/012,490, filed on Jan. 31, 2008.

(51) Int. Cl.
*F25D 23/00* (2006.01)
*G01K 13/00* (2006.01)
(52) U.S. Cl. .......... 374/208; 374/141; 374/33; 374/109; 220/592.2

(58) Field of Classification Search ............ 374/100, 374/141, 29, 30, 31, 32, 33, 34, 35, 36, 37, 374/38, 39, 5, 109, 208, 148; 206/438; 220/592.2
See application file for complete search history.

(56) References Cited

U.S. PATENT DOCUMENTS

| 520,584 | A | | 5/1894 | Turner | |
|---|---|---|---|---|---|
| 2,717,937 | A | * | 9/1955 | Lehr et al. | 337/370 |
| 3,034,845 | A | * | 5/1962 | Haumann | 312/268 |
| 3,069,045 | A | * | 12/1962 | Haumann et al. | 220/592.27 |

(Continued)

FOREIGN PATENT DOCUMENTS

FR 2621685 A * 4/1989

(Continued)

OTHER PUBLICATIONS

U.S. Appl. No. 12/658,579, Deane et al.

(Continued)

*Primary Examiner* — Gail Verbitsky

(57) ABSTRACT

Systems include one or more medicinal storage containers. For example, an integrally thermally sealed medicinal storage container may include one or more segments of at least one ultra efficient insulation material, the one or more segments having one or more surface regions, the one or more segments principally defining at least one storage region, one or more regions of substantially thermally sealed connections between at least one of the one or more surface regions of the one or more segments wherein the one or more regions of substantially thermally sealed connections and the one or more segments form at least one integrally thermally sealed medicinal storage region, one or more thermal variant units, and at least one selectively-operable thermal conduction unit.

17 Claims, 14 Drawing Sheets

U.S. PATENT DOCUMENTS

| | | | |
|---|---|---|---|
| 3,921,844 A | 11/1975 | Walles | |
| 4,003,426 A | 1/1977 | Best et al. | |
| 4,057,029 A | 11/1977 | Seiter | |
| 4,057,101 A | 11/1977 | Ruka et al. | |
| 4,094,127 A | 6/1978 | Romagnoli | |
| 4,184,601 A | 1/1980 | Stewart et al. | |
| 4,312,669 A | 1/1982 | Boffito et al. | |
| 4,358,490 A | 11/1982 | Nagai | |
| 4,388,051 A | 6/1983 | Dresler et al. | |
| 4,402,927 A | 9/1983 | Von Dardel et al. | |
| 4,428,854 A | 1/1984 | Enjo et al. | |
| 4,482,465 A | 11/1984 | Gray | |
| 4,526,015 A | 7/1985 | Laskaris | |
| 4,726,974 A | 2/1988 | Nowobilski et al. | |
| 4,796,432 A | 1/1989 | Fixsen et al. | |
| 4,810,403 A | 3/1989 | Bivens et al. | |
| 4,955,204 A | 9/1990 | Pehl et al. | |
| 4,956,976 A | 9/1990 | Kral et al. | |
| 4,976,308 A | 12/1990 | Faghri | |
| 5,012,102 A | 4/1991 | Gowlett | |
| 5,103,337 A | 4/1992 | Schrenk et al. | |
| 5,116,105 A | 5/1992 | Hong | |
| 5,138,559 A | 8/1992 | Kuehl et al. | |
| 5,245,869 A | 9/1993 | Clarke et al. | |
| 5,261,241 A | 11/1993 | Kitahara et al. | |
| 5,330,816 A | 7/1994 | Rusek, Jr. | |
| 5,355,684 A | 10/1994 | Guice | |
| 5,376,184 A | 12/1994 | Aspden | |
| 5,390,734 A | 2/1995 | Voorhes et al. | |
| 5,444,223 A | 8/1995 | Blama | |
| 5,452,565 A | 9/1995 | Blom et al. | |
| 5,548,116 A | 8/1996 | Pandelisev | |
| 5,563,182 A | 10/1996 | Epstein et al. | |
| 5,580,522 A * | 12/1996 | Leonard et al. | 422/46 |
| 5,590,054 A | 12/1996 | McIntosh | |
| 5,600,071 A | 2/1997 | Sooriakumar et al. | |
| 5,633,077 A | 5/1997 | Olinger | |
| 5,709,472 A | 1/1998 | Prusik et al. | |
| 5,782,344 A | 7/1998 | Edwards et al. | |
| 5,800,905 A | 9/1998 | Sheridan et al. | |
| 5,846,224 A * | 12/1998 | Sword et al. | 604/113 |
| 5,857,778 A | 1/1999 | Ells | |
| 5,900,554 A | 5/1999 | Baba et al. | |
| 5,915,283 A | 6/1999 | Reed et al. | |
| 6,030,580 A | 2/2000 | Raasch et al. | |
| 6,042,264 A | 3/2000 | Prusik et al. | |
| 6,050,598 A | 4/2000 | Upton | |
| 6,209,343 B1 | 4/2001 | Owen | |
| 6,212,904 B1 * | 4/2001 | Arkharov et al. | 62/615 |
| 6,213,339 B1 | 4/2001 | Lee | |
| 6,234,341 B1 | 5/2001 | Tattam | |
| 6,272,679 B1 * | 8/2001 | Norin | 725/62 |
| 6,453,749 B1 | 9/2002 | Petrovic et al. | |
| 6,485,805 B1 | 11/2002 | Smith et al. | |
| 6,571,971 B1 | 6/2003 | Weiler | |
| 6,673,594 B1 | 1/2004 | Owen et al. | |
| 6,692,695 B1 * | 2/2004 | Bronshtein et al. | 422/41 |
| 6,742,673 B2 | 6/2004 | Credle, Jr. et al. | |
| 6,751,963 B2 | 6/2004 | Navedo et al. | |
| 6,771,183 B2 | 8/2004 | Hunter | |
| 6,841,917 B2 | 1/2005 | Potter | |
| 6,877,504 B2 | 4/2005 | Schreff et al. | |
| 6,967,051 B1 | 11/2005 | Augustynowicz et al. | |
| 7,001,656 B2 | 2/2006 | Maignan et al. | |
| 7,240,513 B1 | 7/2007 | Conforti | |
| 7,258,247 B2 | 8/2007 | Marquez | |
| 7,267,795 B2 | 9/2007 | Ammann et al. | |
| 7,278,278 B2 | 10/2007 | Wowk et al. | |
| 7,596,957 B2 | 10/2009 | Fuhr et al. | |
| 2002/0050514 A1 | 5/2002 | Schein | |
| 2002/0083717 A1 | 7/2002 | Mullens et al. | |
| 2002/0084235 A1 | 7/2002 | Lake | |
| 2002/0130131 A1 | 9/2002 | Zucker et al. | |
| 2003/0072687 A1 * | 4/2003 | Nehring et al. | 422/102 |
| 2003/0148773 A1 | 8/2003 | Spriestersbach et al. | |
| 2004/0035120 A1 | 2/2004 | Brunnhofer | |
| 2004/0055313 A1 | 3/2004 | Navedo et al. | |
| 2004/0055600 A1 * | 3/2004 | Izuchukwu | 128/205.15 |
| 2004/0103302 A1 | 5/2004 | Yoshimura et al. | |
| 2005/0009192 A1 | 1/2005 | Page | |
| 2005/0067441 A1 * | 3/2005 | Alley | 222/547 |
| 2005/0247312 A1 * | 11/2005 | Davies | 128/203.15 |
| 2005/0274378 A1 * | 12/2005 | Bonney et al. | 128/200.23 |
| 2006/0021355 A1 | 2/2006 | Boesel et al. | |
| 2006/0071585 A1 | 4/2006 | Wang | |
| 2006/0191282 A1 | 8/2006 | Sekiya et al. | |
| 2006/0196876 A1 | 9/2006 | Rohwer | |
| 2006/0259188 A1 | 11/2006 | Berg | |
| 2007/0041814 A1 | 2/2007 | Lowe | |
| 2008/0269676 A1 * | 10/2008 | Bieberich et al. | 604/113 |
| 2009/0275478 A1 | 11/2009 | Atkins et al. | |
| 2009/0301125 A1 * | 12/2009 | Myles et al. | 62/323.1 |
| 2010/0016168 A1 | 1/2010 | Atkins et al. | |
| 2010/0028214 A1 * | 2/2010 | Howard et al. | 422/102 |
| 2010/0213200 A1 * | 8/2010 | Deane et al. | 220/592.2 |
| 2010/0287963 A1 * | 11/2010 | Billen et al. | 62/126 |
| 2011/0117538 A1 * | 5/2011 | Niazi | 435/5 |

FOREIGN PATENT DOCUMENTS

| | | | |
|---|---|---|---|
| GB | 2441636 A * | 3/2008 | |
| WO | WO 99/036725 A1 | 7/1999 | |

OTHER PUBLICATIONS

Adams, R. O.; "A review of the stainless steel surface"; The Journal of Vacuum Science and Technology A; Bearing a date of Jan.-Mar. 1983; pp. 12-18; vol. 1, No. 1; American Vacuum Society.

Bartl, J., et al.; "Emissivity of aluminium and its importance for radiometric measurement"; Measurement Science Review; Bearing a date of 2004; pp. 31-36; vol. 4, Section 3.

Beavis, L. C.; "Interaction of Hydrogen with the Surface of Type 304 Stainless Steel"; The Journal of Vacuum Science and Technology; Bearing a date of Mar.-Apr. 1973; pp. 386-390; vol. 10, No. 2; American Vacuum Society.

Benvenuti, C., et al.; "Pumping characteristics of the St707 nonevaporable getter (Zr 70 V 24.6-Fe 5.4 wt %)"; The Journal of Vacuum Science and Technology A; Bearing a date of Nov.-Dec. 1996; pp. 3278-3282; vol. 14, No. 6; American Vacuum Society.

Demko, J. A., et al.; "Design Tool for Cryogenic Thermal Insulation Systems"; Advances in Cryogenic Engineering: Transactions of the Cryogenic Engineering Conference-CEC; Bearing a date of 2008; pp. 145-151; vol. 53; American Institute of Physics.

Hedayat, A., et al.; "Variable Density Multilayer Insulation for Cryogenic Storage"; Contract NAS8-40836; 36$^{th}$ Joint Propulsion Conference; Bearing a date of Jul. 17-19, 2000; pp. 1-10.

Horgan, A. M., et al.; "Hydrogen and Nitrogen Desorption Phenomena Associated with a Stainless Steel 304 Low Energy Electron Diffraction (LEED) and Molecular Beam Assembly"; The Journal of Vacuum Science and Technology; Bearing a date of Jul.-Aug. 1972; pp. 1218-1226; vol. 9, No. 4.

Keller, C. W., et al.; "Thermal Performance of Multilayer Insulations, Final Report, Contract NAS 3-14377"; Bearing a date of Apr. 5, 1974; pp. 1-446.

Kishiyama, K., et al.; "Measurement of Ultra Low Outgassing Rates for NLC UHV Vacuum Chambers"; Proceedings of the 2001 Particle Accelerator Conference, Chicago; Bearing a date of 2001; pp. 2195-2197; IEEE.

Little, Arthur D.; "Liquid Propellant Losses During Space Flight, Final Report on Contract No. NASw-615"; Bearing a date of Oct. 1964; pp. 1-315.

Lockheed Missiles & Space Company; "High-Performance Thermal Protection Systems, Contract NAS 8-20758, vol. II"; Bearing a date of Dec. 31, 1969; pp. 1-117.

Nemanič, Vincenc, et al.; "Experiments with a thin-walled stainless-steel vacuum chamber"; The Journal of Vacuum Science and Technology A; Bearing a date of Jul.-Aug. 2000; pp. 1789-1793; vol. 18, No. 4; American Vacuum Society.

Nemanič, Vincenc, et al.; "Outgassing of a thin wall vacuum insulating panel"; Vacuum; Bearing a date of 1998; pp. 233-237; vol. 49, No. 3; Elsevier Science Ltd.

Nemanič, Vincenc, et al.; "A study of thermal treatment procedures to reduce hydrogen outgassing rate in thin wall stainless steel cells"; Vacuum; Bearing a date of 1999; pp. 277-280; vol. 53; Elsevier Science Ltd.

PCT International Search Report; International App. No. PCT/US 09/01715; Jan. 8, 2010; pp. 1-2.

Sasaki, Y. Tito; "A survey of vacuum material cleaning procedures: A subcommittee report of the American Vacuum Society Recommended Practices Committee"; The Journal of Vacuum Science and Technology A; Bearing a date of May-Jun. 1991; pp. 2025-2035; vol. 9, No. 3; American Vacuum Society.

U.S. Department of Health and Human Services, Centers for Disease Control and Prevention; "Recommended Immunization Schedule for Persons Aged 0 Through 6 Years—United States"; Bearing a date of 2009; p. 1.

Vesel, Alenka, et al.; "Oxidation of AISI 304L stainless steel surface with atomic oxygen"; Applied Surface Science; Bearing a date of 2002; pp. 94-103; vol. 200; Elsevier Science B.V.

Young, J. R.; "Outgassing Characteristics of Stainless Steel and Aluminum with Different Surface Treatments"; The Journal of Vacuum Science and Technology; Bearing a date of Oct. 14, 1968; pp. 398-400; vol. 6, No. 3.

Zajec, Bojan, et al.; "Hydrogen bulk states in stainless-steel related to hydrogen release kinetics and associated redistribution phenomena"; Vacuum; Bearing a date of 2001; pp. 447-452; vol. 61; Elsevier Science Ltd.

PCT International Search Report; International App. No. PCT/US08/13646; Apr. 9, 2009; pp. 1-2.

PCT International Search Report; International App. No. PCT/US08/13648; Mar. 13, 2009; pp. 1-2.

PCT International Search Report; International App. No. PCT/US08/13642; Feb. 26, 2009; pp. 1-2.

PCT International Search Report; International App. No. PCT/US08/13643; Feb. 20, 2009; pp. 1-2.

U.S. Appl. No. 12/220,439, Hyde et al.
U.S. Appl. No. 12/152,467, Bowers et al.
U.S. Appl. No. 12/152,465, Bowers et al.
U.S. Appl. No. 12/927,982, Deane et al.
U.S. Appl. No. 12/927,981, Chou et al.

Chen, Dexiang, et al.; "Opportunities and challenges of developing thermostable vaccines"; Expert Reviews Vaccines; 2009; pp. 547-557; vol. 8, No. 5; Expert Reviews Ltd.

Greenbox Systems; "Thermal Management System"; 2010; Printed on: Feb. 3, 2011; p. 1 of 1; located at http://www.greenboxsystems.com.

Matthias, Dipika M., et al.; "Freezing temperatures in the vaccine cold chain: A systematic literature review"; Vaccine; 2007; pp. 3980-3986; vol. 25; Elsevier Ltd.

Pure Temp; "Technology"; Printed on: Feb. 9, 2011; p. 1-3; located at http://puretemp.com/technology.html.

Spur Industries Inc.; "The Only Way to Get Them Apart is to Melt Them Apart"; 2006; pp. 1-3; located at http://www.spurind.com/applications.php.

Williams, Preston; "Greenbox Thermal Management System Refrigerate-able 2 to 8 C Shipping Containers"; Printed on: Feb. 9, 2011; p. 1; located at http://www.puretemp.com/documents/Refrigerate-able%202%20to%208%20C%20Shipping%20Containers.pdf.

Wirkas, Theo, et al.; "A vaccine cold chain freezing study in PNG highlights technology needs for hot climate countries"; Vaccine; 2007; pp. 691-697; vol. 25; Elsevier Ltd.

World Health Organization; "Preventing Freeze Damage to Vaccines: Aide-memoire for prevention of freeze damage to vaccines"; 2007; pp. 1-4; WHO/IVB/07.09; World Health Organization.

World Health Organization; "Temperature sensitivity of vaccines"; Department of Immunization, Vaccines and Biologicals, World Health Organization; Aug. 2006; pp. 1-62 plus cover sheet, pp. i-ix, and end sheet (73 pages total); WHO/IVB/06.10; World Health Organization.

U.S. Appl. No. 12/012,490, Hyde et al.
U.S. Appl. No. 12/008,695, Hyde et al.
U.S. Appl. No. 12/006,089, Hyde et al.
U.S. Appl. No. 12/006,088, Hyde et al.
U.S. Appl. No. 12/001,757, Hyde et al.

3M Monitor Mark™; "Time Temperature Indicators—Providing a visual history of time temperature exposure"; 3M Microbiology; bearing a date of 2006; pp. 1-4; located at 3M.com/microbiology.

Arora, Anubhav; Hakim, Itzhak; Baxter, Joy; Rathnasingham, Ruben; Srinivasan, Ravi; Fletcher, Daniel A.; "Needle-Free Delivery of Macromolecules Across the Skin by Nanoliter-Volume Pulsed Microjets"; PNAS Applied Biological Sciences; Mar. 13, 2007; pp. 4255-4260; vol. 104; No. 11; The National Academy of Sciences USA.

Bang, Abhay T.; Bang, Rani A.; Baitule, Sanjay B.; Reddy, M. Hanimi; Deshmukh, Mahesh D.; "Effect of Home-Based Neonatal Care and Management of Sepsis on Neonatal Mortality: Field Trial in Rural India"; The Lancet; Dec. 4, 1999; pp. 1955-1961; vol. 354; SEARCH (Society for Education, Action, and Research in Community Health).

Brenzel, Logan; Wolfson, Lara J.; Fox-Rushby, Julia; Miller, Mark; Halsey, Neal A.; "Vaccine-Preventable Diseases—Chapter 20"; Disease Control Priorities in Developing Countries; printed on Oct. 15, 2007; pp. 389-411.

CDC; "Vaccine Management: Recommendations for Storage and Handling of Selected Biologicals"; Jan. 2007; 16 pages total; Department of Health & Human Services U.S.A.

Chiritescu, Catalin; Cahill, David G.; Nguyen, Ngoc; Johnson, David; Bodapati, Arun; Keblinski, Pawel; Zschack, Paul; "Ultralow Thermal Conductivity in Disordered, Layered WSe2 Crystals; Science"; Jan. 19, 2007; pp. 351-353; vol. 315; The American Association for the Advancement of Science.

Cohen, Sharon; Hayes, Janice S. Tordella, Tracey; Puente, Ivan; "Thermal Efficiency of Prewarmed Cotton, Reflective, and Forced—Warm-Air Inflatable Blankets in Trauma Patients"; International Journal of Trauma Nursing; Jan.-Mar. 2002; pp. 4-8; vol. 8; No. 1; The Emergency Nurses Association.

Cole-Palmer; "Temperature Labels and Crayons"; www.coleparmer.com; bearing a date of 1971 and printed on Sep. 27, 2007; p. 1.

Cornell University Coop; "The Food Keeper"; printed on Oct. 15, 2007; 7 pages total (un-numbered).

Daryabeigi, Kamran; "Thermal Analysis and Design Optimization of Multilayer Insulation for Reentry Aerodynamic Heating"; Journal of Spacecraft and Rockets; Jul.-Aug. 2002; pp. 509-514; vol. 39; No. 4; American Institute of Aeronautics and Astronautics Inc.

Department of Health and Social Services, Division of Public Health, Section of Community Health and EMS, State of Alaska; Cold Injuries Guidelines—Alaska Multi-Level 2003 Version; bearing dates of 2003 and Jan. 2005; pp. 1-60; located at http://www.chems.alaska.gov.

Ette, Ene I.; "Conscience, the Law, and Donation of Expired Drugs"; The Annals of Pharmacotherapy; Jul./Aug. 2004; pp. 1310-1313; vol. 38.

Ferrotec; "Ferrofluid: Magnetic Liquid Technology"; bearing dates of 2001-2008; printed on Mar. 10, 2008; found at http://www.ferrotec.com/technology/ferrofluid.php.

Fricke, Jochen; Emmerling, Andreas; "Aerogels—Preparation, Properties, Applications"; Structure and Bonding; 1992; pp. 37-87; vol. 77; Springer-Verlag Berlin Heidelberg.

JAMC; "Preventing Cold Chain Failure: Vaccine Storage and Handling"; JAMC; Oct. 26, 2004; p. 1050; vol. 171; No. 9; Canadian Medical Association.

Jorgensen, Pernille; Chanthap, Lon; Rebueno, Antero; Tsuyuoka, Reiko; Bell, David; "Malaria Rapid Diagnostic Tests in Tropical Climates: The Need for a Cool Chain"; American Journal of Tropical Medicine and Hygiene; 2006; pp. 750-754; vol. 74; No. 5; The American Society of Tropical Medicine and Hygiene.

Levin, Carol E.; Nelson, Carib M.; Widjaya, Anton; Moniaga, Vanda; Anwar, Chairiyah; "The Costs of Home Delivery of a Birth Dose of Hepatitis B Vaccine in a Prefilled Syringe in Indonesia"; Bulletin of the World Health Organization; Jun. 2005; pp. 456-461 + 1 pg. Addenda; vol. 83; No. 6.

Llanos-Cuentas, A.; Campos, P.; Clendenes, M.; Canfield. C.J.; Hutchinson, D.B.A.; "Atovaquone and Proguanil Hydrochloride Compared with Chloroquine or Pyrimethamine/Sulfadoxine for Treatment of Acute Plasmodium Falciparum Malaria in Peru"; The Brazilian Journal of Infectious Diseases; 2001; pp. 67-72; vol. 5; No. 2; The Brazilian Journal of Infectious Diseases and Contexto Publishing.

Lockman, Shahin; Ndase, P.; Holland, D.; Shapiro, R.; Connor, J.; Capparelli, E.; "Stability of Didanosine and Stavudine Pediatric Oral Solutions and Kaletra Capsules at Temperatures from 4°C to 55°C"; 12th Conference on Retroviruses and Opportunistic Infections, Boston, Massachusetts; Feb. 22-25, 2005; p. 1; Foundation for Retrovirology and Human Health.

Ma, Kun-Quan; and Liu, Jing; "Nano liquid-metal fluid as ultimate coolant"; Physics Letters A; bearing dates of Jul. 10, 2006, Sep. 9, 2006, Sep. 18, 2006, Sep. 26, 2006, and Jan. 29, 2007; pp. 252-256; vol. 361, Issue 3; Elsevier B.V.

Moonasar, Devanand; Goga, Ameena Ebrahim; Frean, John; Kruger, Philip; Chandramohan; Daniel; "An Exploratory Study of Factors that Affect the Performance and Usage of Rapid Diagnostic Tests for Malaria in the Limpopo Province, South Africa"; Malaria Journal; Jun. 2007; pp. 1-5; vol. 6; No. 74; Moonasar et al.; licensee BioMed Central Ltd.

Moshfegh, B.; "A New Thermal Insulation System for Vaccine Distribution; Journal of Thermal Insulation"; Jan. 1992; pp. 226-247; vol. 15; Technomic Publishing Co., Inc.

Nolan, Timothy D. C.; Hattler, Brack G.; Federspiel, William J.; "Development of a Balloon Volume Sensor for Pulsating Balloon Catheters"; ASAIO Journal; 2004; pp. 225-233; vol. 50; No. 3; American Society of Artificial Internal Organs.

PATH—A Catalyst for Global Health; "Uniject™ Device—The Radically Simple Uniject™ Device—Rethinking the Needle to Improve Immunization"; bearing dates of 1995-2006; printed on Oct. 11, 2007; pp. 1-2; located at http://www.path.org/projects/uniject.php; PATH Organization.

Pau, Alice K.; Moodley, Neelambal K.; Holland, Diane T.; Fomundam, Henry; Matchaba, Gugu U.; and Capparelli, Edmund V.; "Instability of lopinavir/ritonavir capsules at ambient temperatures in sub-Saharan Africa: relevance to WHO antiretroviral guidelines"; AIDS; Bearing dates of 2005, Mar. 29, 2005, and Apr. 20, 2005; pp. 1229-1236; vol. 19, No. 11; Lippincott Williams & Wilkins.

Pekala, R. W.; "Organic Aerogels From the Polycondensation of Resorcinol With Formaldehyde"; Journal of Materials Science; Sep. 1989; pp. 3221-3227; vol. 24; No. 9; Springer Netherlands.

Pickering, Larry K.; Wallace, Gregory; Rodewald, Lance; "Too Hot, Too Cold: Issues with Vaccine Storage"; Pediatrics®—Official Journal of the American Academy of Pediatrics; 2006; pp. 1738-1739 (4 pages total, incl. cover sheet and end page); vol. 118; American Academy of Pediatrics.

Post, Richard F.; "Maglev: A New Approach"; Scientific American; Jan. 2000; pp. 82-87; Scientific American, Inc.

Program for Appropriate Technology in Health (PATH); "The Radically Simple Uniject Device"; PATH—Reflections on Innovations in Global Health; printed on Jan. 26, 2007; pp. 1-4; located at www.path.org.

Reeler, Anne V.; Simonsen, Lone; Health Access International; "Unsafe Injections, Fatal Infections"; Bill and Melinda Gates Children's Vaccine Program Occasional Paper #2; May 2000; pp. 1-8; located at www.ChildrensVaccine.org/html/safe_injection.htm.

Risha, Peter G.; Shewiyo, Danstan; Msami, Amani; Masuki, Gerald; Vergote, Geert; Vervaet, Chris; Remon, Jean Paul; "In vitro Evaluation of the Quality of Essential Drugs on the Tanzanian Market"; Tropical Medicine and International Health; Aug. 2002; pp. 701-707; vol. 7; No. 8; Blackwell Science Ltd.

Seto, Joyce; Marra, Fawziah; "Cold Chain Management of Vaccines"; Continuing Pharmacy Professional Development Home Study Program; Feb. 2005; pp. 1-19; University of British Columbia.

Shockwatch; "Environmental Indicators"; printed on Sep. 27, 2007; pp. 1-2; located at www.shockwatch.com.

Suttmeier, Chris; "Warm Mix Asphalt: A Cooler Alternative"; Material Matters—Around the Hot Mix Industry; Spring 2006; pp. 21-22; Peckham Materials Corporation.

Thompson, Marc T.; "Eddy current magnetic levitation—Models and experiments"; IEEE Potentials; Feb./Mar. 2000; pp. 40-46; IEEE.

"Two Wire Gage / Absolute Pressure Transmitters—Model 415 and 440"; Honeywell Sensotec; pp. 1-2; Located at www.sensotec.com and www.honeywell.com/sensing.

UNICEF Regional Office for Latin America & the Carribean (UNICEF-TACRO); Program for Appropriate Technology in Health (PATH); "Final Report Cold Chain Workshop," Panama City, May 31-Jun. 2, 2006; pp. 1-4 plus cover sheet, table of contents, and annexes A, B and C (22 pages total).

World Health Organization; "Getting started with vaccine vial monitors; Vaccines and Biologicals"; World Health Organization; Dec. 2002; pp. 1-20 plus cover sheets, end sheet, contents pages, abbreviations page; revision history page and acknowledgments page (29 pages total); World Health Organization; located at www.who.int/vaccines-documents.

World Health Organization; "Getting started with vaccine vial monitors—Questions and answers on field operations"; Technical Session on Vaccine Vial Monitors, Mar. 27, 2002, Geneva; pp. 1-17 (p. 2 left intentionally blank); World Health Organization.

Yamakage, Michiaki; Sasaki, Hideaki; Jeong, Seong-Wook; Iwasaki, Sohshi; Namiki, Akiyoshi; "Safety and Beneficial Effect on Body Core Temperature of Prewarmed Plasma Substitute Hydroxyethyl Starch During Anesthesia" [Abstract]; Anesthesiology; 2004; p. A-1285; vol. 101; ASA.

Zhu, Z. Q.; Howe, D.; "Halbach Permanent Magnet Machines and Applications: A Review"; IEE Proceedings—Electric Power Applications; Jul. 2001; pp. 299-308; vol. 148; No. 4; University of Sheffield, Department of Electronic & Electrical Engineering, Sheffield, United Kingdom.

Bapat, S. L. et al.; "Experimental investigations of multilayer insulation"; Cryogenics; Bearing a date of Aug. 1990; pp. 711-719; vol. 30.

Bapat, S. L. et al.; "Performance prediction of multilayer insulation"; Cryogenics; Bearing a date of Aug. 1990; pp. 700-710; vol. 30.

Barth, W. et al.; "Experimental investigations of superinsulation models equipped with carbon paper"; Cryogenics; Bearing a date of May 1988; pp. 317-320; vol. 28.

Barth, W. et al.; "Test results for a high quality industrial superinsulation"; Cryogenics; Bearing a date of Sep. 1988; pp. 607-609; vol. 28.

Benvenuti, C. et al.; "Obtention of pressures in the $10^{-14}$ torr range by means of a Zr V Fe non evaporable getter"; Vacuum; Bearing a date of 1993; pp. 511-513; vol. 44; No. 5-7; Pergamon Press Ltd.

Benvenuti, C.; "Decreasing surface outgassing by thin film getter coatings"; Vacuum; Bearing a date of 1998; pp. 57-63; vol. 50; No. 1-2; Elsevier Science Ltd.

Benvenuti, C.; "Nonevaporable getter films for ultrahigh vacuum applications"; Journal of Vacuum Science Technology A Vacuum Surfaces, and Films; Bearing a date of Jan./Feb. 1998; pp. 148-154; vol. 16; No. 1; American Chemical Society.

Berman, A.; "Water vapor in vacuum systems"; Vacuum; Bearing a date of 1996; pp. 327-332; vol. 47; No. 4; Elsevier Science Ltd.

Bernardini, M. et al.; "Air bake-out to reduce hydrogen outgassing from stainless steel"; Journal of Vacuum Science Technology; Bearing a date of Jan./Feb. 1998; pp. 188-193; vol. 16; No. 1; American Chemical Society.

Bo, H. et al.; "Tetradecane and hexadecane binary mixtures as phase change materials (PCMs) for cool storage in district cooling systems"; Energy; Bearing a date of 1999; vol. 24; pp. 1015-1028; Elsevier Science Ltd.

Boffito, C. et al.; "A nonevaporable low temperature activatable getter material"; Journal of Vacuum Science Technology; Bearing a date of Apr. 1981; pp. 1117-1120; vol. 18; No. 3; American Vacuum Society.

Brown, R.D.; "Outgassing of epoxy resins in vacumm."; Vacuum; Bearing a date of 1967; pp. 25-28; vol. 17; No. 9; Pergamon Press Ltd.

Burns, H. D.; "Outgassing Test for Non-metallic Materials Associated with Sensitive Optical Surfaces in a Space Environment"; MSFC-SPEC-1443; Bearing a date of Oct. 1987; pp. 1-10.

Chen, G. et al.; "Performance of multilayer insulation with slotted shield"; Cryogenics ICEC Supplement; Bearing a date of 1994; pp. 381-384; vol. 34.

Chen, J. R. et al.; "An aluminum vacuum chamber for the bending magnet of the SRRC synchrotron light source"; Vacuum; Bearing a date of 1990; pp. 2079-2081; vol. 41; No. 7-9; Pergamon Press PLC.

Chen, J. R. et al.; "Outgassing behavior of A6063-EX aluminum alloy and SUS 304 stainless steel"; Journal of Vacuum Science Technology; Bearing a date of Nov./Dec. 1987; pp. 3422-3424; vol. 5; No. 6; American Vacuum Society.

Chen, J. R. et al.; "Outgassing behavior on aluminum surfaces: Water in vacuum systems"; *Journal of Vacuum Science Technology*; Bearing a date of Jul./Aug. 1994; pp. 1750-1754; vol. 12; No. 4; American Vacuum Society.

Chen, J. R. et al.; "Thermal outgassing from aluminum alloy vacuum chambers"; *Journal of Vacuum Science Technology*; Bearing a date of Nov./Dec. 1985; pp. 2188-2191; vol. 3; No. 6; American Vacuum Society.

Chen, J. R.; "A comparison of outgassing rate of 304 stainless steel and A6063-EX aluminum alloy vacuum chamber after filling with water"; *Journal of Vacuum Science Technology A Vacuum Surfaces and Film*; Bearing a date of Mar. 1987; pp. 262-264; vol. 5; No. 2; American Chemical Society.

Chiggiato, P.; "Production of extreme high vacuum with non evaporable getters" *Physica Scripta*; Bearing a date of 1997; pp. 9-13; vol. T71.

Cho, B.; "Creation of extreme high vacuum with a turbomolecular pumping system: A baking approach"; *Journal of Vacuum Science Technology*; Bearing a date of Jul./Aug. 1995; pp. 2228-2232; vol. 13; No. 4; American Vacuum Society.

Choi, S. et al.; "Gas permeability of various graphite/epoxy composite laminates for cryogenic storage systems"; *Composites Part B: Engineering*; Bearing a date of 2008; pp. 782-791; vol. 39; Elsevier Science Ltd.

Chun, I. et al.; "Effect of the Cr-rich oxide surface on fast pumpdown to ultrahigh vacuum"; *Journal of Vacuum Science Technology A Vacuum, Surfaces, and Films*; Bearing a date of Sep./Oct. 1997; pp. 2518-2520; vol. 15; No. 5; American Vacuum Society.

Chun, I. et al.; "Outgassing rate characteristic of a stainless-steel extreme high vacuum system"; *Journal of Vacuum Science Technology*; Bearing a date of Jul./Aug. 1996; pp. 2636-2640; vol. 14; No. 4; American Vacuum Society.

Crawley, D J. et al.; "Degassing Characteristics of Some 'O' Ring Materials"; *Vacuum*; Bearing a date of 1963; pp. 7-9; vol. 14; Pergamon Press Ltd.

Csernatony, L.; "The Properties of Viton 'A' Elastomers II. The influence of permeation, diffusion and solubility of gases on the gas emission rate from an O-ring used as an atmospheric seal or high vacuum immersed"; *Vacuum*; Bearing a date of 1965; pp. 129-134; vol. 16; No. 3; Pergamon Press Ltd.

Day, C.; "The use of active carbons as cryosorbent"; *Colloids and Surfaces A Physicochemical and Engineering Aspects*; Bearing a date of 2001; pp. 187-206; vol. 187-188; Elsevier Science.

Della Porta, P.; "Gas problem and gettering in sealed-off vacuum devices"; *Vacuum*; Bearing a date of 1996; pp. 771-777; vol. 47; No. 6-8 Elsevier Science Ltd.

Dylla, H. F. et al.; "Correlation of outgassing of stainless steel and aluminum with various surface treatments"; *Journal of Vacuum Science Technology*; Bearing a date of Sep./Oct. 1993; pp. 2623-2636; vol. 11; No. 5; American Vacuum Society.

Elsey, R. J. "Outgassing of vacuum material I"; *Vacuum*; Bearing a date of 1975; pp. 299-306; vol. 25; No. 7; Pergamon Press Ltd.

Elsey, R. J. "Outgassing of vacuum materials II" *Vacuum*; Bearing a date of 1975; pp. 347-361; vol. 25; No. 8; Pergamon Press Ltd.

Engelmann, G. et al.; "Vacuum chambers in composite material"; *Journal of Vacuum Science Technology*; Bearing a date of Jul./Aug. 1987; pp. 2337-2341; vol. 5; No. 4; American Vacuum Society.

Eyssa, Y. M. et al.; "Thermodynamic optimization of thermal radiation shields for a cryogenic apparatus"; *Cryogenics*; Bearing a date of May 1978; pp. 305-307; vol. 18; IPC Business Press.

Glassford, A. P. M. et al.; "Outgassing rate of multilayer insulation"; 1978; Bearing a date of 1978; pp. 83-106.

Gupta, A. K. et al.; "Outgassing from epoxy resins and methods for its reduction"; *Vacuum*; Bearing a date of 1977; pp. 61-63; vol. 27; No. 12; Pergamon Press Ltd.

Halaczek, T. et al.; "Flat-plate cryostat for measurements of multilayer insulation thermal conductivity"; *Cryogenics*; Bearing a date of Oct. 1985; pp. 593-595; vol. 25; Butterworth & Co. Ltd.

Halaczek, T. et al.; "Unguarded cryostat for thermal conductivity measurements of multilayer insulations"; *Cryogenics*; Bearing a date of Sep. 1985; pp. 529-530; vol. 25; Butterworth & Co. Ltd.

Halaczek, T. L. et al.; "Heat transport in self-pumping multilayer insulation"; *Cryogenics*; Bearing a date of Jun. 1986; pp. 373-376; vol. 26; Butterworth & Co. Ltd.

Halaczek, T. L. et al.; "Temperature variation of thermal conductivity of self- pumping multilayer insulation"; *Cryogenics*; Bearing a date of Oct. 1986; pp. 544-546.; vol. 26; Butterworth & Co. Ltd.

Halldórsson, Arni, et al.; "The sustainable agenda and energy efficiency: Logistics solutions and supply chains in times of climate change"; *International Journal of Physical Distribution & Logistics Management*; Bearing a date of 2010; pp. 5-13; vol. 40; No. ½; Emerald Group Publishing Ltd.

Halliday, B. S.; "An introduction to materials for use in vacuum"; *Vacuum*; Bearing a date of 1987; pp. 583-585; vol. 37; No. 8-9; Pergamon Journals Ltd.

Hirohata, Y.; "Hydrogen desorption behavior of aluminium materials used for extremely high vacuum chamber"; *Journal of Vacuum Science Technology*; Bearing a date of Sep./Oct. 1993; pp. 2637-2641; vol. 11; No. 5; American Vacuum Society.

Holtrop, K. L. et al.; "High temperature outgassing tests on materials used in the DIII-D tokamak"; *Journal of Vacuum Science Technology*; Bearing a date of Jul./Aug. 2006; pp. 1572-; vol. 24; No. 4; American Vacuum Society.

Hong, S. et al.; "Investigation of gas species in a stainless steel ultrahigh vacuum chamber with hot cathode ionization gauges"; *Measurement Science and Technology*; Bearing a date of 2004; pp. 359-364; vol. 15; IOP Science.

Ishikawa, Y. et al.; "Reduction of outgassing from stainless surfaces by surface oxidation"; *Vacuum*; Bearing a date of 1990; pp. 1995-1997; vol. 4; No. 7-9; Pergamon Press PLC.

Ishikawa, Y.; "An overview of methods to suppress hydrogen outgassing rate from austenitic stainless steel with reference to UHV and EXV"; *Vacuum*; Bearing a date of 2003; pp. 501-512; vol. 69; No. 4; Elsevier Science Ltd.

Ishimaru, H. et al.; "All Aluminum Alloy Vacuum System for the TRISTAN e+ e− Storage"; *IEEE Transactions on Nuclear Science*; Bearing a date of Jun. 1981; pp. 3320-3322; vol. NS-28; No. 3.

Ishimaru, H. et al.; "Fast pump-down aluminum ultrahigh vacuum system"; *Journal of Vacuum Science Technology*; Bearing a date of May/Jun. 1992; pp. 547-552 ; vol. 10; No. 3; American Vacuum Society.

Ishimaru, H. et al.; "Turbomolecular pump with an ultimate pressure of $10^{-12}$ Torr"; *Journal of Vacuum Science Technology*; Bearing a date of Jul./Aug. 1994; pp. 1695-1698; vol. 12; No. 4; American Vacuum Society.

Ishimaru, H.; "All-aluminum-alloy ultrahigh vacuum system for a large-scale electron—positron collider"; *Journal of Vacuum Science Technology*; Bearing a date of Jun. 1984; pp. 1170-1175; vol. 2; No. 2; American Vacuum Society.

Ishimaru, H.; "Aluminium alloy-sapphire sealed window for ultrahigh vacuum"; *Vacuum*; Bearing a date of 1983; pp. 339-340.; vol. 33; No. 6; Pergamon Press Ltd.

Ishimaru, H.; "Bakeable aluminium vacuum chamber and bellows with an aluminium flange and metal seal for ultra-high vacuum"; *Journal of Vacuum Science Technology*; Bearing a date of Nov./Dec. 1978; pp. 1853-1854; vol. 15; No. 6; American Vacuum Society.

Ishimaru, H.; "Ultimate pressure of the order of $10^{-13}$ Torr in an aluminum alloy vacuum chamber"; *Journal of Vacuum Science and Technology*; Bearing a date of May/Jun. 1989; pp. 2439-2442; vol. 7; No. 3; American Vacuum Society.

Jacob, S. et al.; "Investigations into the thermal performance of multilayer insulation (300-77 K) Part 2: Thermal analysis"; *Cryogenics*; Bearing a date of 1992; pp. 1147-1153; vol. 32; No. 12; Butterworth-Heinemann Ltd.

Jacob, S. et al.; "Investigations into the thermal performance of multilayer insulation (300-77 K) Part 1: Calorimetric studies"; *Cryogenics*; Bearing a date of 1992; pp. 1137-1146; vol. 32; No. 12; Butterworth-Heinemann Ltd.

Jenkins, C. H. M.; "Gossamer spacecraft: membrane and inflatable structures technology for space applications"; AIAA; Bearing a date of 2000; pp. 503-527; vol. 191.

Jhung, K. H. C. et al.; "Achievement of extremely high vacuum using a cryopump and conflat aluminium"; *Vacuum*; Bearing a date of 1992; pp. 309-311; vol. 43; No. 4; Pergamon Press PLC.

Kato, S. et al.; "Achievement of extreme high vacuum in the order of $10^{-10}$ Pa without baking of test chamber"; *Journal of Vacuum Science Technology*; Bearing a date of May/Jun. 1990; pp. 2860-2864; vol. 8; No. 3; American Vacuum Society.

Keller, K. et al.; "Application of high temperature multilayer insulations"; *Acta Astronautica*; Bearing a date of 1992; pp. 451-458; vol. 26; No. 6; Pergamon Press Ltd.

Koyatsu, Y. et al. "Measurements of outgassing rate from copper and copper alloy chambers"; *Vacuum*; Bearing a date of 1996; pp. 709-711; vol. 4; No. 6-8; Elsevier Science Ltd.

Kristensen, D. et al.; "Stabilization of vaccines: Lessons learned"; *Human Vaccines*; Bearing a date of Mar. 2010; pp. 227-231; vol. 6; No. 3; Landes Bioscience.

Kropschot, R. H.; "Multiple layer insulation for cryogenic applications"; *Cryogenics*; Bearing a date of Mar. 1961; pp. 135-135; vol. 1.

Li, Y.; "Design and pumping characteristics of a compact titanium—vanadium non-evaporable getter pump"; *Journal of Vacuum Science Technology*; Bearing a date of May/Jun. 1998; pp. 1139-1144; vol. 16; No. 3; American Vacuum Society.

Liu, Y. C. et al.; "Thermal outgassing study on aluminum surfaces"; *Vacuum*; Bearing a date of 1993; pp. 435-437; vol. 44; No. 5-7; Pergamon Press Ltd.

Londer, H. et al.; "New high capacity getter for vacuum insulated mobile $LH_2$ storage tank systems"; *Vacuum*; Bearing a date of 2008; pp. 431-434; vol. 82; No. 4; Elsevier Ltd.

Matsuda, A. et al.; "Simple structure insulating material properties for multilayer insulation"; *Cryogenics*; Bearing a date of Mar. 1980; pp. 135-138; vol. 20; IPC Business Press.

Mikhalchenko, R. S. et al.; "Study of heat transfer in multilayer insulations based on composite spacer materials."; *Cryogenics*; Bearing a date of Jun. 1983; pp. 309-311; vol. 23; Butterworth & Co. Ltd.

Mikhalchenko, R. S. et al.; "Theoretical and experimental investigation of radiative-conductive heat transfer in multilayer insulation"; *Cryogenics*; Bearing a date of May 1985; pp. 275-278; vol. 25; Butterworth & Co. Ltd.

Miki, M. et al.; "Characteristics of extremely fast pump-down process in an aluminum ultrahigh vacuum system"; *Journal of Vacuum Science Technology*; Bearing a date of Jul./Aug. 1994; pp. 1760-1766; vol. 12; No. 4; American Vacuum Society.

Mohri, M. et al.; "Surface study of Type 6063 aluminium alloys for vacuum chamber materials"; *Vacuum*; Bearing a date of 1984; pp. 643-647; vol. 34; No. 6; Pergamon Press Ltd.

Mukugi, K. et al.; "Characteristics of cold cathode gauges for outgassing measurements in uhv range"; *Vacuum*; Bearing a date of 1993; pp. 591-593; vol. 44; No. 5-7; Pergamon Press Ltd.

Nemanič, V. et al.; "Anomalies in kinetics of hydrogen evolution from austenitic stainless steel from 300 to 1000°C"; *Journal of Vacuum Science Technology*; Bearing a date of Jan./Feb. 2001; pp. 215-222; vol. 19; No. 1; American Vacuum Society.

Nemanič, V. et al.; "Outgassing in thin wall stainless steel cells"; *Journal of Vacuum Science Technology*; Bearing a date of May/Jun. 1999; pp. 1040-1046; vol. 17; No. 3; American Vacuum Society.

Nemanič, V.; "Outgassing of thin wall stainless steel chamber"; *Vacuum*; Bearing a date of 1998; pp. 431-437; vol. 50; No. 3-4; Elsevier Science Ltd.

Nemanič, V.; "Vacuum insulating panel"; *Vacuum*; bearing a date of 1995; pp. 839-842; vol. 46; No. 8-10; Elsevier Science Ltd.

Odaka, K. et al.;"Effect of baking temperature and air exposure on the outgassing rate of type 316L stainless steel"; *Journal of Vacuum Science Technology*; Bearing a date of Sep./Oct. 1987; pp. 2902-2906; vol. 5; No. 5; American Vacuum Society.

Odaka, K.; "Dependence of outgassing rate on surface oxide layer thickness in type 304 stainless steel before and after surface oxidation in air"; *Vacuum*; Bearing a date of 1996; pp. 689-692; vol. 47; No. 6-8; Elsevier Science Ltd.

Okamura, S. et al.; "Outgassing measurement of finely polished stainless steel"; *Journal of Vacuum Science Technology*; Bearing a date of Jul./Aug. 1991; pp. 2405-2407; vol. 9; No. 4; American Vacuum Society.

Patrick, T. J.; "Outgassing and the choice of materials for space instrumentation"; *Vacuum*; Bearing a date of 1973; pp. 411-413; vol. 23; No. 11; Pergamon Press Ltd.

Patrick, T. J.; "Space environment and vacuum properties of spacecraft materials"; *Vacuum*; Bearing a date of 1981; pp. 351-357; vol. 31; No. 8-9; Pergamon Press Ltd.

Poole, K. F. et al.; "Hialvac and Teflon outgassing under ultra-high vacuum conditions"; *Vacuum*; Bearing a date of Jun. 30, 1980; pp. 415-417; vol. 30; No. 10; Pergamon Press Ltd.

Redhead, P. A.; "Recommended practices for measuring and reporting outgassing data"; *Journal of Vacuum Science Technology*; Bearing a date of Sep./Oct. 2002; pp. 1667-1675; vol. 20; No. 5; American Vacuum Society.

Rutherford, S; "The Benefits of Viton Outgassing"; Bearing a date of 1997; pp. 1-5; Duniway Stockroom Corp.

Saito, K. et al.; "Measurement system for low outgassing materials by switching between two pumping paths"; *Vacuum*; Bearing a date of 1996; pp. 749-752; vol. 47; No. 6-8; Elsevier Science Ltd.

Saitoh, M. et al.; "Influence of vacuum gauges on outgassing rate measurements" ; *Journal of Vacuum Science Technology*; Bearing a date of Sep./Oct. 1993; pp. 2816-2821; vol. 11; No. 5; American Vacuum Society.

Santhanam, S. M. T. J. et al. ;"Outgassing rate of reinforced epoxy and its control by different pretreatment methods"; *Vacuum*; Bearing a date of 1978; pp. 365-366; vol. 28; No. 8-9; Pergamon Press Ltd.

Sasaki, Y. T.; "Reducing SS 304/316 hydrogen outgassing to $2\times10^{-15}$torr $1/cm^2s$"; *Journal of Vacuum Science Technology*; Bearing a date of Jul./Aug. 2007; pp. 1309-1311; vol. 25; No. 4; American Vacuum Society.

Scurlock, R. G. et al.; "Development of multilayer insulations with thermal conductivities below 0.1 $\mu W\ cm^{-1}\ K^{-1}$"; *Cryogenics*; Bearing a date of May 1976; pp. 303-311; vol. 16.

Setia, S. et al.; "Frequency and causes of vaccine wastage"; *Vaccine* ; Bearing a date of 2002; pp. 1148-1156; vol. 20; Elsevier Science Ltd.

Shu, Q. S. et al.; "Heat flux from 277 to 77 K through a few layers of multilayer insulation"; *Cryogenics*; Bearing a date of Dec. 1986; pp. 671-677; vol. 26; Butterworth & Co. Ltd.

Shu, Q. S. et al.; "Systematic study to reduce the effects of cracks in multilayer insulation Part 1: Theoretical model"; *Cryogenics*; Bearing a date of May 1987; pp. 249-256; vol. 27; Butterworth & Co. Ltd.

Shu, Q. S. et al.; "Systematic study to reduce the effects of cracks in multilayer insulation Part 2: experimental results"; *Cryogenics*; Bearing a date of Jun. 1987; pp. 298-311; vol. 27; No. 6; Butterworth & Co. Ltd.

Suemitsu, M. et al.; "Development of extremely high vacuums with mirror-polished Al-alloy chambers"; *Vacuum*; Bearing a date of 1993; pp. 425-428; vol. 44; No. 5-7; Pergamon Press Ltd.

Suemitsu, M. et al.; "Ultrahigh-vacuum compatible mirror-polished aluminum-alloy surface: Observation of surface-roughness-correlated outgassing rates"; *Journal of Vacuum Science Technology*; Bearing a date of May/Jun. 1992; pp. 570-572; vol. 10; No. 3; American Vacuum Society.

Tatenuma, K. et al.; "Acquisition of clean ultrahigh vacuum using chemical treatment"; *Journal of Vacuum Science Technology*; Bearing a date of Jul./Aug. 1998; pp. 2693-2697; vol. 16; No. 4; American Vacuum Society.

Tatenuma, K.; "Quick acquisition of clean ultrahigh vacuum by chemical process technology"; *Journal of Vacuum Science Technology*; Bearing a date of Jul./Aug. 1993; pp. 2693-2697; vol. 11; No. 4; American Vacuum Society.

Tripathi, A. et al.; "Hydrogen intake capacity of ZrVFe alloy bulk getters"; *Vacuum*; Bearing a date of Aug. 6, 1997; pp. 1023-1025; vol. 48; No. 12; Elsevier Science Ltd.

Watanabe, S. et al.; "Reduction of outgassing rate from residual gas analyzers for extreme high vacuum measurements"; *Journal of Vacuum Science Technology*; Bearing a date of Nov./Dec. 1996; pp. 3261-3266; vol. 14; No. 6; American Vacuum Society.

Wiedemann, C. et al.; "Multi-layer Insulation Literatures Review"; *Advances*; Printed on May 2, 2011; pp. 1-10; German Aerospace Center.

Yamazaki, K. et al.; "High-speed pumping to UHV"; *Vacuum* ; Bearing a date of 2010; pp. 756-759; vol. 84; Elsevier Science Ltd.

Zalba, B. et al.; "Review on thermal energy storage with phase change: materials, heat transfer analysis and applications"; *Applied Thermal Engineering*; Bearing a date of 2003; pp. 251-283; vol. 23; Elsevier Science Ltd.

Zhitomirskij, I.S. et al.; "A theoretical model of the heat transfer processes in multilayer insulation"; *Cryogenics*; Bearing a date of May 1979; pp. 265-268; IPC Business Press.

U.S. Appl. No. 13/200,555, Chou et al.

U.S. Appl. No. 13/199,439, Hyde et al.

Saes Getters; "St707 Getter Alloy for Vacuum Systems"; printed on Sep. 22, 2011; pp. 1-2; located at http://www.saegetters.com/default.aspx?idPage=212.

PCT International Search Report; International App. No. PCT/US 11/00234; Jun. 9, 2011; pp. 1-4.

U.S. Appl. No. 13/135,126, Deane et al.

Cabeza, L. F. et al.; "Heat transfer enhancement in water when used as PCM in thermal energy storage"; Applied Thermal Engineering; 2002; pp. 1141-1151; vol. 22; Elsevier Science Ltd.

Chen, Dexiang et al.; "Characterization of the freeze sensitivity of a hepatitis B vaccine"; Human Vaccines; Jan. 2009; pp. 26-32; vol. 5, Issue 1; Landes Bioscience.

Edstam, James S. et al.; "Exposure of hepatitis B vaccine to freezing temperatures during transport to rural health centers in Mongolia"; Preventive Medicine; 2004; pp. 384-388; vol. 39; The Institute for Cancer Prevention and Elsevier Inc.

Efe, Emine et al.; "What do midwives in one region in Turkey know about cold chain?"; Midwifery; 2008; pp. 328-334; vol. 24; Elsevier Ltd.

Günter, M. M. et al.; "Microstructure and bulk reactivity of the nonevaporable getter $Zr_{57}V_{36}Fe_7$"; J. Vac. Sci. Technol. A; Nov./Dec. 1998; pp. 3526-3535; vol. 16, No. 6; American Vacuum Society.

Hipgrave, David B. et al.; "Immunogenicity of a Locally Produced Hepatitis B Vaccine With the Birth Dose Stored Outside the Cold Chain in Rural Vietnam"; Am. J. Trop. Med. Hyg.; 2006; pp. 255-260; vol. 74, No. 2; The American Society of Tropical Medicine and Hygiene.

Hipgrave, David B. et al.; "Improving birth dose coverage of hepatitis B vaccine"; Bulletin of the World Health Organization; Jan. 2006; pp. 65-71; vol. 84, No. 1; World Health Organization.

Hobson, J. P. et al.; "Pumping of methane by St707 at low temperatures"; J. Vac. Sci. Technol. A; May/Jun. 1986; pp. 300-302; vol. 4, No. 3; American Vacuum Society.

Kendal, Alan P. et al.; "Validation of cold chain procedures suitable for distribution of vaccines by public health programs in the USA"; Vaccine; 1997; pp. 1459-1465; vol. 15, No. 12/13; Elsevier Science Ltd.

Khemis, O. et al.; "Experimental analysis of heat transfers in a cryogenic tank without lateral insulation"; Applied Thermal Engineering; 2003; pp. 2107-2117; vol. 23; Elsevier Ltd.

Li, Yang et al.; "Study on effect of liquid level on the heat leak into vertical cryogenic vessels"; Cryogenics; 2010; pp. 367-372; vol. 50; Elsevier Ltd.

Magennis, Teri et al. "Pharmaceutical Cold Chain: A Gap in the Last Mile—Part 1. Wholesaler/Distributer: Missing Audit Assurance"; Pharmaceutical & Medical Packaging News; Sep. 2010; pp. 44, 46-48, and 50; pmpnews.com.

Matolin, V. et al.; "Static SIMS study of TiZrV NEG activation"; Vacuum; 2002; pp. 177-184; vol. 67; Elsevier Science Ltd.

Nelson, Carib M. et al.; "Hepatitis B vaccine freezing in the Indonesian cold chain: evidence and solutions"; Bulletin of the World Health Organization; Feb. 2004; pp. 99-105 (plus copyright page); vol. 82, No. 2; World Health Organization.

Ren, Qian et al.; "Evaluation of an Outside-The-Cold-Chain Vaccine Delivery Strategy in Remote Regions of Western China"; Public Health Reports; Sep.-Oct. 2009; pp. 745-750; vol. 124.

Rogers, Bonnie et al.; "Vaccine Cold Chain—Part 1. Proper Handling and Storage of Vaccine"; AAOHN Journal; 2010; pp. 337-344 (plus copyright page); vol. 58, No. 8; American Association of Occupational Health Nurses, Inc.

Rogers, Bonnie et al.; Vaccine Cold Chain—Part 2. Training Personnel and Program Management; AAOHN Journal; 2010; pp. 391-402 (plus copyright page); vol. 58, No. 9; American Association of Occupational Health Nurses, Inc.

Techathawat, Sirirat et al.; "Exposure to heat and freezing in the vaccine cold chain in Thailand"; Vaccine; 2007; p. 1328-1333; vol. 25; Elsevier Ltd.

Thakker, Yogini et al.; "Storage of Vaccines in the Community: Weak Link in the Cold Chain?"; British Medical Journal; Mar. 21, 1992; pp. 756-758; vol. 304, No. 6829; BMJ Publishing Group.

Wang, Lixia et al.; "Hepatitis B vaccination of newborn infants in rural China: evaluation of a village-based, out-of-cold-chain delivery strategy"; Bulletin of the World Health Organization; Sep. 2007; pp. 688-694; vol. 85, No. 9; World Health Organization.

Wei, Wei et al.; "Effects of structure and shape on thermal performance of Perforated Multi-Layer Insulation Blankets"; Applied Thermal Engineering; 2009; pp. 1264-1266; vol. 29; Elsevier Ltd.

World Health Organization; "Guidelines on the international packaging and shipping of vaccines"; Department of Immunization, Vaccines and Biologicals; Dec. 2005; 40 pages; WHO/IVB/05.23.

Chinese State Intellectual Property Office; First Office Action; App No. 200880119918.0; Jul. 13, 2011.

U.S. Appl. No. 13/385,088, Hyde et al.

U.S. Appl. No. 13/374,218, Hyde et al.

PCT International Search Report; Application No. PCT/US2011/001939; Mar. 27, 2012; pp. 1-2.

* cited by examiner

TEMPERATURE-STABILIZED MEDICINAL STORAGE SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/001,757, entitled TEMPERATURE-STABILIZED STORAGE CONTAINERS, naming Roderick A. Hyde; Edward K. Y. Jung; Nathan P. Myhrvold; Clarence T. Tegreene; William H. Gates, III; Charles Whitmer; and Lowell L. Wood, Jr. as inventors, filed Dec. 11, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,088, entitled TEMPERATURE-STABILIZED STORAGE CONTAINERS WITH DIRECTED ACCESS, naming Roderick A. Hyde; Edward K. Y. Jung; Nathan P. Myhrvold; Clarence T. Tegreene; William H. Gates, III; Charles Whitmer; and Lowell L. Wood, Jr. as inventors, filed Dec. 27, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,089, entitled TEMPERATURE-STABILIZED STORAGE SYSTEMS, naming Roderick A. Hyde; Edward K. Y. Jung; Nathan P. Myhrvold; Clarence T. Tegreene; William H. Gates, III; Charles Whitmer; and Lowell L. Wood, Jr. as inventors, filed Dec. 27, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/008,695, entitled TEMPERATURE-STABILIZED STORAGE CONTAINERS FOR MEDICINALS, naming Roderick A. Hyde; Edward K. Y. Jung; Nathan P. Myhrvold; Clarence T. Tegreene; William H. Gates, III; Charles Whitmer; and Lowell L. Wood, Jr. as inventors, filed Jan. 10, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/012,490, entitled METHODS OF MANUFACTURING TEMPERATURE-STABILIZED STORAGE CONTAINERS, naming Roderick A. Hyde; Edward K. Y. Jung; Nathan P. Myhrvold; Clarence T. Tegreene; William H. Gates, III; Charles Whitmer; and Lowell L. Wood, Jr. as inventors, filed Jan. 31, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Systems include at least one integrally thermally sealed medicinal container, including one or more segments of at least one ultra efficient insulation material, the one or more segments having one or more surface regions, the one or more segments principally defining at least one storage region, one or more regions of substantially thermally sealed connections between at least one of the one or more surface regions of the one or more segments wherein the one or more regions of substantially thermally sealed connections and the one or more segments form at least one integrally thermally sealed medicinal storage region, one or more thermal variant units, and at least one selectively-operable thermal conduction unit between the at least one integrally thermally sealed medicinal storage region and at least one of the one or more thermal variant units. In addition to the foregoing, other aspects are described in the claims, drawings and text forming a part of the present disclosure.

Some aspects include at least one temperature-stabilized medicinal storage container, including at least one medicinal storage structure, including one or more segments of at least one first ultra efficient insulation material shaped to define at least one substantially temperature-stabilized medicinal storage region, one or more thermal variant units, and at least one selectively-operable thermal conduction unit between one or more of the at least one substantially temperature-stabilized medicinal storage region and at least one of the one or more thermal variant units, and at least one access structure, including at least one conduit connecting the at least one substantially temperature-stabilized medicinal storage region and at least one external region of the container, at least one segment of first thermal conduction barrier material surrounding the region of the at least one conduit that connects to the at least one external region of the container; and at least one cover including at least one segment of second thermal conduction barrier material substantially conforming to the at least one segment of first thermal conduction barrier material, wherein the at least one cover includes at least one second ultra efficient insulation material. In addition to the foregoing, other aspects are described in the claims, drawings and text forming a part of the present disclosure.

Some aspects include at least one temperature-stabilized medicinal storage container, including a structural assembly including one or more sections of ultra efficient insulation material primarily defining at least one substantially thermally sealed medicinal storage region, an outlet assembly including one or more outlet channels, wherein the one or more outlet channels are arranged to provide controllable egress of a quantity of a stored material from the at least one substantially thermally sealed medicinal storage region, and the one or more outlet channels substantially follow an extended thermal pathway, one or more thermal variant units, and at least one selectively-operable thermal conduction unit between one or more of the at least one substantially temperature-stabilized medicinal storage region and at least one of the one or more thermal variant units. In addition to the foregoing, other aspects are described in the claims, drawings and text forming a part of the present disclosure.

Some aspects include at least one temperature-stabilized medicinal storage container, including at least one medicinal storage structure, including one or more segments of at least one ultra efficient insulation material shaped to define at least one substantially temperature-stabilized medicinal storage region, one or more thermal variant units, and at least one selectively-operable thermal conduction unit between one or more of the at least one substantially temperature-stabilized medicinal storage region and at least one of the one or more thermal variant units, and at least one access region, including at least one region of the one or more segments of an ultra efficient insulation material configured for at least one perforation by at least one perforation device, wherein one or more of the at least one perforation is configured to provide for a controlled egress of a quantity of a medicinal material from the at least one substantially temperature-stabilized medicinal storage region. In addition to the foregoing, other aspects are described in the claims, drawings and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
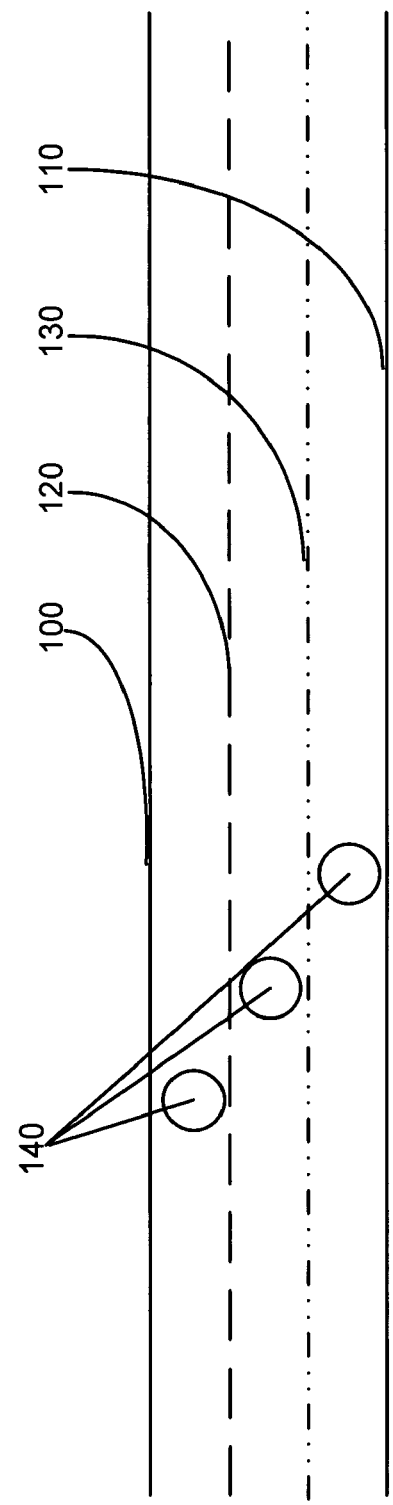
FIG. 1 is a schematic of some aspects of an ultra efficient insulation material, such as multilayer insulation material.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In some aspects, systems include at least one integrally thermally sealed medicinal storage container, including one or more segments of at least one ultra efficient insulation material, the one or more segments having one or more surface regions, the one or more segments principally defining at least one storage region, one or more regions of substantially thermally sealed connections between at least one of the one or more surface regions of the one or more segments wherein the one or more regions of substantially thermally sealed connections and the one or more segments form at least one integrally thermally sealed medicinal storage region, one or more thermal variant units, and at least one selectively-operable thermal conduction unit between the at least one integrally thermally sealed medicinal storage region and at least one of the one or more thermal variant units. An integrally thermally sealed medicinal storage container, such as the ones depicted in FIGS. 2, 3, 4, and 5, includes ultra efficient insulation material principally defining at least one integrally thermally sealed medicinal storage region. An integrally thermally sealed medicinal storage container, such as the ones depicted in FIGS. 2, 3, 4, and 5, includes at least one integrally thermally sealed medicinal storage region with extremely low heat conductance and extremely low heat radiation transfer between the outside environment of the container and the area internal to the at least one integrally thermally sealed medicinal storage region. An integrally sealed medicinal storage container may have virtually zero heat conductance and virtually zero heat radiation transfer between the outside environment of the container and the inside of the at least one integrally thermally sealed medicinal storage region. As used herein, "integrally sealed" refers to containers that are constituently sealed, for example a container that must be broken open to access the contents of the least one integrally thermally sealed medicinal storage region. In some embodiments, an integrally thermally sealed medicinal storage container may be refurbished or repaired and reused, while in other embodiments an integrally thermally sealed medicinal storage container may be designed for single-use and be disposable.

In some aspects, a temperature-stabilized medicinal storage container includes at least one medicinal storage structure, including one or more segments of at least one first ultra efficient insulation material shaped to define at least one substantially temperature-stabilized medicinal storage region, one or more thermal variant units, and at least one selectively operable thermal conduction unit between one or more of the at least one substantially temperature-stabilized medicinal storage region and at least one of the one or more thermal variant units, and at least one access structure, including at least one conduit connecting the at least one substantially temperature-stabilized medicinal storage region and at least one external region of the container, at least one segment of first thermal conduction barrier material surrounding the region of the at least one conduit that connects to the at least one external regions of the container, and at least one cover including at least one segment of second thermal conduction barrier material substantially conforming to the at least one segment of first thermal conduction barrier material, wherein the at least one cover includes at least one second ultra efficient insulation material. A temperature-stabilized medicinal storage container, such as those depicted in FIGS. 6A, 6B, 7 and 8, may be configured to allow for controllable ingress of material into at least one medicinal storage structure. For example, in some embodiments a temperature-stabilized medicinal storage container may be refurbished or repaired and reused, including the addition of medicinal units into at least one storage structure. A temperature-stabilized medicinal storage container may, in some embodiments, be refurbished or repaired and reused in conjunction with the addition, removal or recharge of one or more heat sink units. A temperature-stabilized medicinal storage container may, in some embodiments, be refurbished or repaired and reused in conjunction with the addition or removal of one or more removable inserts within one or more of the at least one storage structure.

In some aspects, a temperature-stabilized medicinal storage container includes a structural assembly including one or more sections of ultra efficient insulation material primarily defining at least one substantially thermally sealed medicinal storage region, an outlet assembly including one or more outlet channels, wherein the one or more outlet channels are arranged to provide controllable egress of a quantity of a stored material from the at least one substantially thermally sealed medicinal storage region, and the one or more outlet channels substantially follow an extended thermal pathway, one or more thermal variant units, and at least one selectively-operable thermal conduction unit between one or more of the at least one substantially temperature-stabilized medicinal storage region and at least one of the one or more thermal variant units. A temperature-stabilized medicinal storage container, such as those depicted in FIGS. 9A, 9B and 9C, may include one or more outlet channels that substantially follow an extended thermal pathway within the structure of the container. In some embodiments, one or more outlet channels may substantially follow an extended thermal pathway that is in whole or in part external to the structure of the container. In some embodiments, the one or more outlet channels that substantially follow an extended thermal pathway may be integral to the container and in other embodiments one or more outlet channels may be removable, detachable or replaceable.

In some aspects, a temperature-stabilized medicinal storage container includes at least one medicinal storage structure, including one or more segments of at least one ultra efficient insulation material shaped to define at least one substantially temperature-stabilized medicinal storage region, one or more thermal variant units, and at least one selectively-operable thermal conduction unit between one or more of the at least one substantially temperature-stabilized medicinal storage region and at least one of the one or more thermal variant units, and least one access region, including at least one region of the one or more segments of an ultra efficient insulation material configured for at least one perforation by at least one perforation device, wherein one or more of the at least one perforation is configured to provide for a controlled egress of a quantity of a medicinal material from the at least one substantially temperature-stabilized medicinal storage region. A temperature-stabilized medicinal storage container, such as those depicted in FIGS. 10, 11, and 12, may include containers including an access region with at least one region of one or more segments of ultra efficient insulation material configured for at least one perforation by at least one perforation device. Some embodiments may include at least one thermally-insulated cover, including a sealing portion positioned for mating to the at least one access region. For example, a thermally-insulated cover may include ultra efficient insulation material. In some embodiments, a medicinal storage container including an access region may be single-use and disposable, while in other embodiments a medicinal storage container including an access region may be repaired or refurbished and reused. For example, a medicinal storage container including an access region may include an access region which is, in whole or in part, replaceable, repairable, may be refurbished, or which may be resealed after perforation by a perforation device. An access region may be resealed, for example, with a thermally-insulated sealable cover, which may be located externally to the container or internally to the container.

The term "medicinal", as used herein, includes a drug, composition, formulation, material or compound intended for medicinal or therapeutic use. For example, a medicinal may include drugs, vaccines, therapeutics, vitamins, pharmaceuticals, remedies, homeopathic agents, naturopathic agents, or treatment modalities in any form, combination or configuration. For example, a medicinal may include vaccines, such as: a vaccine packaged as an oral dosage compound, vaccine within a prefilled syringe, a container or vial containing vaccine, vaccine within a unijet device, or vaccine within an externally deliverable unit (e.g. a vaccine patch for transdermal applications). For example, a medicinal may include treatment modalities, such as: antibody therapies, small-molecule compounds, anti-inflammatory agents, therapeutic drugs, vitamins, or pharmaceuticals in any form, combination or configuration. A medicinal may be in the form of a liquid, gel, solid, semi-solid, vapor, or gas. In some embodiments, a medicinal may be a composite. For example, a medicinal may include a bandage or patch infused with antibiotics, anti-inflammatory agents, coagulants, neurotrophic agents, angiogenic agents, vitamins or pharmaceutical agents.

The term "ultra efficient insulation material," as used herein, may include one or more type of insulation material with extremely low heat conductance and extremely low heat radiation transfer between the surfaces of the insulation material. The ultra efficient insulation material may include, for example, one or more layers of thermally reflective film, high vacuum, aerogel, low thermal conductivity bead-like units, disordered layered crystals, low density solids, or low density foam. In some embodiments, the ultra efficient insulation material includes one or more low density solids such as aerogels, such as those described in, for example: Fricke and Emmerling, Aerogels-preparation, properties, applications, Structure and Bonding 77: 37-87 (1992); and Pekala, Organic aerogels from the polycondensation of resorcinol with formaldehyde, Journal of Materials Science 24: 3221-3227 (1989); each of which are herein incorporated by reference. As used herein, "low density" may include materials with density from about 0.01 g/cm$^3$ to about 0.10 g/cm$^3$, and materials with density from about 0.005 g/cm$^3$ to about 0.05 g/cm$^3$. In some embodiments, the ultra efficient insulation material includes one or more layers of disordered layered crystals, such as those described in, for example: Chiritescu et al., Ultralow thermal conductivity in disordered, layered WSe$_2$ crystals, Science 315: 351-353 (2007), which is herein incorporated by reference. In some embodiments, the ultra efficient insulation material includes at least two layers of thermal reflective film separated, for example, by at least one of: high vacuum, low thermal conductivity spacer units, low thermal conductivity bead like units, or low density foam. For example, the ultra-efficient insulation material may include at least one multiple layer insulating composite such as described in U.S. Pat. No. 6,485,805 to Smith et al., titled "Multilayer insulation composite," which is herein incorporated by reference. For example, the ultra-efficient insulation material may include at least one metallic sheet insulation system, such as that described in U.S. Pat. No. 5,915,283 to Reed et al., titled "Metallic sheet insulation system," which is herein incorporated by reference. For example, the ultra-efficient insulation material may include at least one thermal insulation system, such as that described in U.S. Pat. No. 6,967,051 to Augustynowicz et al., titled "Thermal insulation systems," which is herein incorporated by reference. For example, the ultra-efficient insulation material may include at least one rigid multilayer material for thermal insulation, such as that described in U.S. Pat. No. 7,001,656 to Maignan et al., titled "Rigid multilayer material for thermal insulation," which is herein incorporated by reference.

In reference now to FIG. 1, in some embodiments, an ultra efficient insulation material may include at least one multilayer insulation material. For example, an ultra efficient insulation material may include multilayer insulation material such as that used in space program launch vehicles, including by NASA. See, e.g., Daryabeigi, Thermal analysis and design optimization of multilayer insulation for reentry aerodynamic heating, Journal of Spacecraft and Rockets 39: 509-514 (2002), which is herein incorporated by reference. As illustrated in FIG. 1, in some embodiments, an ultra efficient insulation material may include a multilayer insulation material including at least two layers of thermal reflective film 120, 130 separated by low thermal conductivity spacer units 140. The low thermal conductivity spacer units may include, for example, low thermal conductivity bead-like structures, aerogel particles, folds or inserts of thermal reflective film. Although two layers of thermal reflective film are shown in FIG. 1, in some embodiments there may be one layer of thermal reflective film or more than two layers of thermal reflective film. Similarly, there may be variable numbers of low thermal conductivity spacer units 140. In some embodiments there may be one or more additional layers within or in addition to the multilayer insulation material, such as, for example, an outer structural layer 100 or an inner structural layer 110. An inner or an outer structural layer may be made of any material appropriate to the embodiment, for example an inner or an outer structural layer may include: plastic, metal, alloy, composite, or glass. In some embodiments, there may be one or more layers of high vacuum between layers of thermal reflective film.

Some embodiments may include at least one superinsulation material. For example, in some embodiments, an ultra efficient insulation material includes at least one material described above and at least one superinsulation material. As used herein, a "superinsulation material" may include structures wherein at least two floating thermal radiation shields exist in an evacuated double-wall annulus, closely spaced but thermally separated by at least one poor-conducting fiber-like material.

In some embodiments, an ultra efficient insulation material includes at least two layers of thermal reflective material separated from each other by magnetic suspension. The layers of thermal reflective material may be separated, for example, by magnetic suspension methods including magnetic induction suspension or ferromagnetic suspension. For more information regarding magnetic suspension systems, see Thompson, Eddy current magnetic levitation models and experiments, IEEE Potentials, February/March 2000, 40-44, and Post, Maglev: a new approach, Scientific American, January 2000, 82-87, which are each incorporated herein by reference. Ferromagnetic suspension may include, for example, the use of magnets with a Halbach field distribution. For more information regarding Halbach machine topologies and related applications suitable for use in an embodiment described herein, see Zhu and Howe, Halbach permanent magnet machines and applications: a review, IEE Proc.-Electr. Power Appl. 148: 299-308 (2001), which is herein incorporated by reference.

The term "heat sink unit," as used herein, includes one or more units that absorb thermal energy, such as that described, for example, in U.S. Pat. No. 5,390,734 to Voorhes et al., titled "Heat Sink," U.S. Pat. No. 4,057,101 to Ruka et al., titled "Heat Sink," U.S. Pat. No. 4,003,426 to Best et al., titled "Heat or Thermal Energy Storage Structure," and U.S. Pat. No. 4,976,308 to Faghri titled "Thermal Energy Storage Heat Exchanger," which are each incorporated herein by reference. Heat sink units may include, for example: units containing frozen water or other types of ice; units including frozen material that is generally gaseous at ambient temperature and pressure, such as frozen carbon dioxide ($CO_2$); units including liquid material that is generally gaseous at ambient temperature and pressure, such as liquid nitrogen; units including artificial gels or composites with heat sink properties; units including phase change materials; and units including refrigerants, such as that described, for example, in: U.S. Pat. No. 5,261,241 to Kitahara et al., titled "Refrigerant," U.S. Pat. No. 4,810,403 to Bivens et al., titled "Halocarbon Blends for Refrigerant Use," U.S. Pat. No. 4,428,854 to Enjo et al., titled "Absorption Refrigerant Compositions for Use in Absorption Refrigeration Systems," and U.S. Pat. No. 4,482,465 to Gray, titled "Hydrocarbon-Halocarbon Refrigerant Blends," which are each herein incorporated by reference. Some embodiments of containers as described herein may include one or more heat sink units, or some may include no heat sink units. Heat sink units may be thermally coupled to one or more of the at least one storage region. Some embodiments may include one or more type of heat sink units. In some embodiments, heat sink units may be removable, for example they may be removed in conjunction with stored medicinal units or independently. In some embodiments, heat sink units may be replaceable or rechargeable, for example heat sink units containing frozen water or other types of ice or those containing units including artificial gels or composites with heat sink properties that may be refrozen.

The term "active cooling unit," as used herein, includes conductive and radiative cooling mechanisms that require electricity from an external source to operate. For example, active cooling units may include one or more of: actively powered fans, actively pumped refrigerant systems, thermoelectric systems, active heat pump systems, active vapor-compression refrigeration systems and active heat exchanger systems. The external energy required to operate such mechanisms may originate, for example, from municipal electrical power supplies or electric batteries. Some embodiments of containers as described herein may include no active cooling units.

Some embodiments may include one or more regions of elevated thermal transfer within the container. For example, a region of elevated thermal transfer may include a region adjacent to an access region with elevated thermal transfer to an exterior region relative to a substantially temperature-stabilized medicinal storage region. For example, a region of elevated thermal transfer may include a region adjacent to a segment of at least one ultra-efficient insulation material that is, for example, less thick or has fewer layers than other segments of ultra-efficient insulation material, thereby allowing slightly higher heat leak. For example, a region of elevated thermal transfer may include an internal region of the container which is temporarily or consistently at a higher temperature than other regions, such as, for example, a region that is thermally connected to an active cooling unit or is not thermally connected to a heat sink unit.

Some embodiments include one or more selectively-operable thermal conduction units and one or more thermal variant units. As used herein, a "thermal variant unit" may include any unit or region which is consistently or temporarily in a temperature range which is a distinct temperature range from that of one or more other units or regions. For example, a thermal variant unit may include one or more heat sink units, one or more active cooling units, or one or more regions of elevated thermal transfer. A selectively-operable thermal conduction unit may include one or more selectively-operable thermal conduction connections between one or more regions of relatively higher temperature and one or more regions of relatively lower temperature. A selectively-operable thermal conduction unit may, for example, be located between one or more of the at least one substantially temperature-stabilized medicinal storage region and at least one of the one or more thermal variant units. In some embodiments, a selectively operable thermal conduction unit may include at least one bimetallic unit. A bimetallic unit may include at least one metal with a high thermal expansion co-efficient and at least one metal with a low thermal expansion co-efficient. For example, a bimetallic unit may include one or more combinations such as brass and iron, aluminum and iron, or magnesium and zirconium. A bimetallic unit may include at least one material with a high thermal expansion co-efficient and at least one material with a low thermal expansion co-efficient. In some embodiments, a material with a high thermal expansion co-efficient or a material with a low thermal expansion co-efficient may not be metal or metallic. For example, a bimetallic unit may include a plastic film with a metal coating. In some embodiments, a selectively operable thermal conduction unit may include at least one mechanical actuator. In some embodiments, a selectively operable thermal conduction unit may include at least one thermally conductive fluid. For example, a thermally conductive fluid may include mercury, a ferrofluid, or a nanoliquid. For example, ferrofluids are commercially available from Ferrotec, with a United States corporate headquarters in Bedford, N.H. More information regarding ferrofluids may be found in the Ferrofluid: Magnetic Liquid Technology document, which is herein incorporated by reference. More information regarding nanoliquids is available in Ma and Liu, Nano liquid-metal fluid as ultimate coolant, Physics Letters A 361 (2007), pages 252-256, which is herein incorporated by reference. A thermally conductive fluid may be reversibly deployable, for example a thermally conductive fluid may be introduced into a thermal connection unit when desired, and then removed when desired by one or more system parameter or one or more system user.

Figure 5:
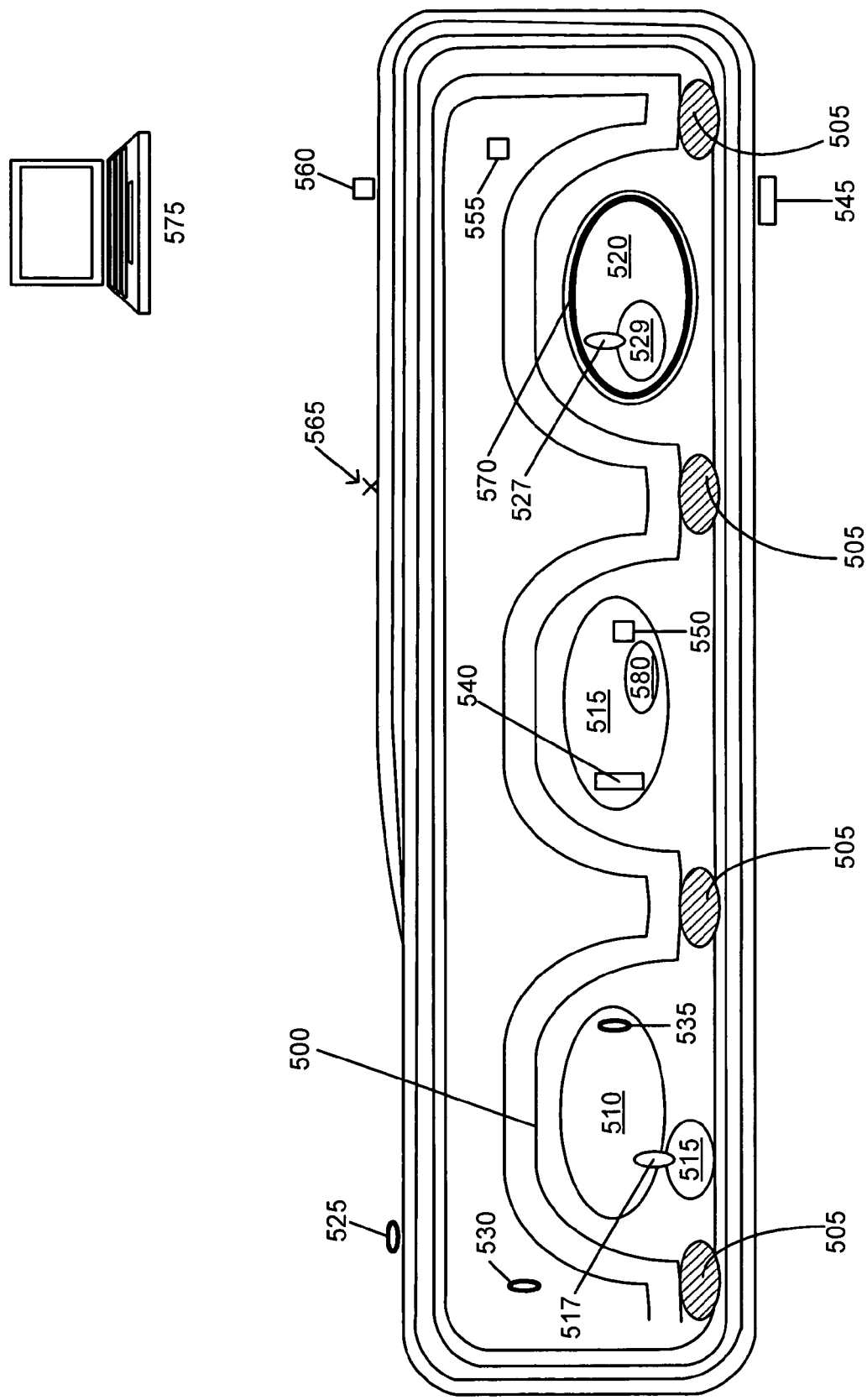
FIG. 5 is a schematic of some aspects of an integrally thermally sealed medicinal storage container.

Some embodiments include at least one layer of nontoxic material on an interior surface of one or more of the at least one medicinal storage region. For example, FIG. 5 depicts nontoxic material 570 within integrally thermally sealed medicinal storage region 520. Nontoxic material may include, for example, material that does not itself react with, or produce residue that may be toxic to, the contents of the at least one medicinal storage region, or material that does not produce residue, or otherwise impart properties to the contents that may be toxic to, the future users of contents of the at least one medicinal storage region. Nontoxic material may include material that maintains the chemical structure of the contents of the at least one medicinal storage region, for example nontoxic material may include chemically inert or non-reactive materials. Nontoxic material may include material that has been developed for use in, for example, medical, pharmaceutical or food storage applications. Nontoxic material may include material that may be cleaned or sterilized, for example material that may be irradiated, autoclaved, or disinfected. Nontoxic material may include material that contains one or more antibacterial, antiviral, antimicrobial, or antipathogen agents. For example, nontoxic material may include aldehydes, hypochlorites, oxidizing agents, phenolics, quaternary ammonium compounds, or silver. Nontoxic material may include material that is structurally stable in the presence of one or more cleaning or sterilizing compounds or radiation, such as plastic that retains its structural integrity after irradiation, or metal that does not oxidize in the presence of one or more cleaning or sterilizing compounds. Nontoxic material may include material that consists of multiple layers, with layers removable for cleaning or sterilization, such as for reuse or refurbishment of the at least one substantially thermally sealed storage region. Nontoxic material may include, for example, material including metals, fabrics, papers or plastics.

Some embodiments include at least one layer of material including at least one metal on an interior surface of one or more of the at least one medicinal storage region. For example, the at least one metal may include gold, aluminum, copper, or silver. The at least one metal may include at least one metal composite or alloy, for example steel, stainless steel, metal matrix composites, gold alloy, aluminum alloy, copper alloy, or silver alloy. In some embodiments, the at least one metal includes metal foil, such as titanium foil, aluminum foil, silver foil, or gold foil. A metal foil may be a component of a composite, such as, for example, in association with polyester film, such as polyethylene terephthalate (PET) polyester film. The at least one layer of material including at least one metal on the interior surface of at least one storage region may include at least one metal that may be sterilized or disinfected. For example, the at least one metal may be sterilized or disinfected using plasmons. For example, the at least one metal may be sterilized or disinfected using autoclaving, thermal means, or chemical means. Depending on the embodiment, the at least one layer of material including at least one metal on an interior surface of at least one medicinal storage region may include at least one metal that has specific heat transfer properties, such as a thermal radiative properties.

In some embodiments, a container includes one or more removable inserts within an interior of one or more of the at least one medicinal storage region. The removable inserts may be made of any material appropriate for the embodiment, including nontoxic materials, metal, alloy, composite, or plastic. The one or more removable inserts may include inserts that may be removed, reused or reconditioned. For example, one or more removable inserts may be removed in conjunction with the removal of at least one medicinal unit. The one or more removable inserts may include inserts that may be cleaned, sterilized, or disinfected as appropriate to the embodiment.

Some embodiments of containers as described herein may include a plurality of storage regions within the container. In some embodiments, an outer assembly including one or more sections of ultra efficient insulation material substantially defines a plurality of medicinal storage regions. The plurality of medicinal storage regions may be, for example, of comparable size and shape or they may be of differing sizes and shapes as appropriate to the embodiment. Different storage regions may include, for example, various removable inserts, at least one layer including at least one metal on an interior surface of a storage region, or at least one layer of nontoxic material on an interior surface, in any combination or grouping.

Some embodiments may include at least one temperature indicator. Temperature indicators may be located at multiple locations relative to the container. For example, FIG. 5 depicts an integrally thermally sealed container including multiple temperature indicators 525, 530, 535. For example, at least one temperature indicator 535 may be located within one or more of the at least one medicinal storage region, at least one temperature indicator 525 may be located exterior to the container, or at least one temperature indicator 530 may be located within the structure of the container. Temperature indicators may include temperature indicating labels, which may be reversible or irreversible. Temperature indicators suitable for some embodiments may include, for example, the Environmental Indicators sold by ShockWatch Company, with headquarters in Dallas Tex., the Temperature Indicators sold by Cole-Palmer Company of Vernon Hills Ill. and the Time Temperature Indicators sold by 3M Company, with corporate headquarters in St. Paul Minn., the brochures for which are each hereby incorporated by reference. Temperature indicators suitable for some embodiments may include time-temperature indicators, such as those described in U.S. Pat. Nos. 5,709,472 and 6,042,264 to Prusik et al., titled "Time-temperature indicator device and method of manufacture" and U.S. Pat. No. 4,057,029 to Seiter, titled "Time-temperature indicator," each of which is herein incorporated by reference. Temperature indicators may include, for example, chemically-based indicators, temperature gauges, thermometers, bimetallic strips, or thermocouples.

In some embodiments, a container such as those described herein may include one or more sensors. Sensors may be located at various positions relative to the container. For example, FIG. 5 depicts an integrally thermally sealed container including sensors 550, 555, 560. At least one sensor 550 may be located within one or more of the at least one integrally thermally sealed medicinal storage region, at least one sensor 560 may be located exterior to the container, or at least one sensor 555 may be located within the structure of the container. In some embodiments, multiple sensors may be located in multiple positions. In some embodiments, the one or more sensors includes at least one sensor of a gaseous pressure within one or more of the at least one storage region, sensor of a mass within one or more of the at least one storage region, sensor of a stored volume within one or more of the at least one storage region, temperature sensor, or sensor of an identity of an item within one or more of the at least one storage region. In some embodiments, at least one sensor may include a temperature sensor, such as, for example, chemical sensors, thermometers, bimetallic strips, or thermocouples. A medicinal storage container may include one or more sensors such as a physical sensor component such as described in U.S. Pat. No. 6,453,749 to Petrovic et al., titled "Physical sensor component," which is herein incorporated by reference. A medicinal storage container may include one or more sensors such as a pressure sensor such as described in U.S. Pat. No. 5,900,554 to Baba et al., titled "Pressure sensor," which is herein incorporated by reference. A medicinal storage container may include one or more sensors such as a vertically integrated sensor structure such as described in U.S. Pat. No. 5,600,071 to Sooriakumar et al., titled "Vertically integrated sensor structure and method," which is herein incorporated by reference. A medicinal storage container may include one or more sensors such as a system for determining a quantity of liquid or fluid within a container, such as described in U.S. Pat. No. 5,138,559 to Kuehl et al., titled "System and method for measuring liquid mass quantity," U.S. Pat. No. 6,050,598 to Upton, titled "Apparatus for and method of monitoring the mass quantity and density of a fluid in a closed container, and a vehicular air bag system incorporating such apparatus," and U.S. Pat. No. 5,245,869 to Clarke et al., titled "High accuracy mass sensor for monitoring fluid quantity in storage tanks," each of which is herein incorporated by reference. A medicinal storage container may include one or more sensors of radio frequency identification ("RFID") tags to identify material within the at least one substantially thermally sealed storage region. RFID tags are well known in the art, for example in U.S. Pat. No. 5,444,223 to Blama, titled "Radio frequency identification tag and method," which is herein incorporated by reference.

Figure 4:
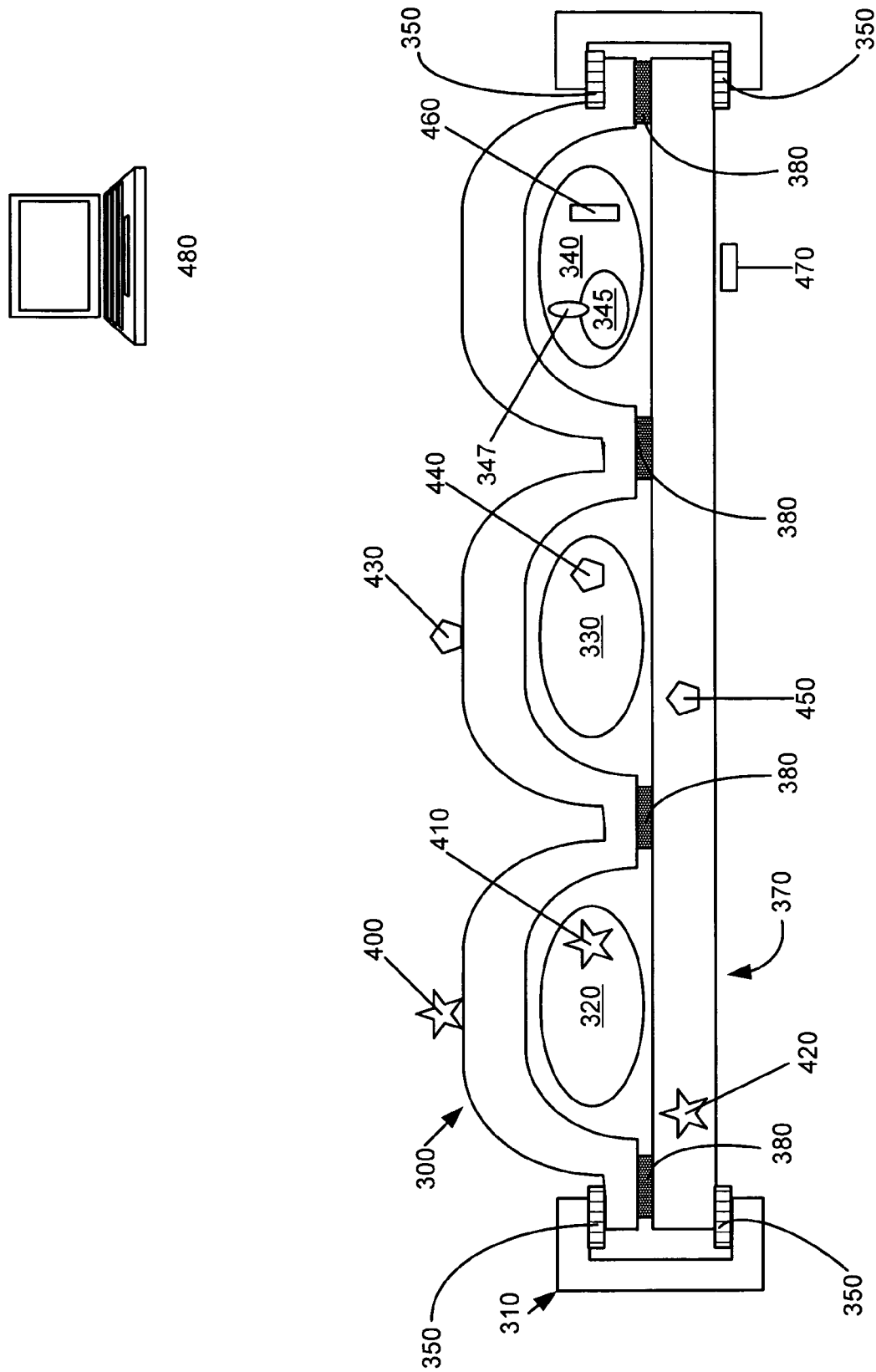
FIG. 4 is a schematic of some aspects of an integrally thermally sealed medicinal storage container.

In some embodiments, a container such as those described herein may include one or more communications devices. The one or more communications devices, may include, for example, one or more recording devices, one or more transmission devices, one or more display devices, or one or more receivers. Communications devices may include, for example, communication devices that allow a user to detect information about the container visually, auditorily, or via signal to a remote device. For example, FIGS. 4 and 5 depict remote display devices 480 and 575. Some embodiments may include more than one type of communications device, and in some embodiments the devices may be operably linked. For example, some embodiments may contain both a receiver and an operably linked transmission device, so that a signal may be received by the receiver which then causes a transmission to be made from the transmission device. Some embodiments may include more than one type of communications device that are not operably linked. For example, some embodiments may include a transmission device and a display device, wherein the transmission device is not operably linked to the display device. Some embodiments may include communications devices on the exterior of the container, including devices attached to the exterior of the container, devices adjacent to the exterior of the container, or devices located at a distance from the exterior of the container. Some embodiments may include communications devices located within the structure of the container. Some embodiments may include communications devices located within at least one of the one or more medicinal storage regions.

Some embodiments include a container including one or more recording devices. The one or more recording devices may include devices that are magnetic, electronic, chemical, or transcription based recording devices. Depending on the embodiment, there may be a single recording device or a plurality of recording devices. For example, FIG. 4 depicts recording devices 400, 410, 420. One or more recording device 410 may be located within one or more of the at least one medicinal storage region, one or more recording device 400 may be located exterior to the container, or one or more recording device 420 may be located within the structure of the container. The one or more recording device may record, for example, the temperature from one or more temperature sensor, the result from one or more temperature indicator, or the gaseous pressure, mass, volume or identity of an item information from at least one sensor within the at least one storage region. In some embodiments, the one or more recording devices may be integrated with one or more sensor. For example, in some embodiments there may be one or more temperature sensors which record the highest, lowest or average temperature detected. For example, in some embodiments, there may be one or more mass sensors which record one or more mass changes within the container over time. For example, in some embodiments, there may be one or more gaseous pressure sensors which record one or more gaseous pressure changes within the container over time.

Some embodiments include a container including one or more transmission device. There may be a single transmission device or a plurality of transmission devices. Transmission devices may be located in a number of positions. For example, FIG. 4 depicts transmission devices 430, 440, 450. One or more transmission device 440 may be located within at least one medicinal storage region, one or more transmission device 430 may be located exterior to the container, or one or more transmission device 450 may be located within the structure of the container. The one or more transmission device may transmit any signal or information, for example, the temperature from one or more temperature sensor, or the gaseous pressure, mass, volume or identity of an item or information from at least one sensor within the at least one storage region. In some embodiments, the one or more transmission device may be integrated with one or more sensor, or one or more recording device. The one or more transmission devices may transmit by any means known in the art, for example, but not limited to, via radio frequency (e.g. RFID tags), magnetic field, electromagnetic radiation, electromagnetic waves, sonic waves, or radioactivity.

In some embodiments an integrally thermally sealed container may include one or more display devices. Display devices may be located at a number of locations relative to the container. For example, with reference to FIGS. 4 and 5, in some embodiments, the one or more display devices 460, 540 may be located within one or more of the at least one substantially thermally sealed storage region. In some embodiments, the one or more display devices 470, 545 may be located on the exterior of the container. In some embodiments, one or more display devices may be integrated with one or more sensor. For example, in some embodiments one or more display devices may show temperature information. In some embodiments, one or more display devices may be integrated with one or more recording devices. For example, a recording device may include a visual printing, such as a graph, which is visualized with a display device, such as a window-like covering. For example, a recording device may include a digital display which indicates some aspects of the information being recorded in real-time or over a time interval. In some embodiments, the one or more display devices 480, 575 may be located at a distance from the container. For example, one or more display devices located at a distance from the container 480, 575 may display data transmitted from one or more transmission device. Display devices located at a distance may include, for example, electronic displays or computer displays. In some embodiments, data from one or more transmission device may be stored in an analog or digital medium for later display to a user. For example, data transmitted from one or more transmission device may be stored on a remote computer system for display at a later time as requested by a system or a user.

In some embodiments, an integrally thermally sealed container may include one or more receivers. For example, one or more receivers may include devices that detect sonic waves, electromagnetic waves, radio signals, electrical signals, magnetic pulses, or radioactivity. Depending on the embodiment, one or more receiver may be located within one or more of the at least one substantially thermally sealed storage region. In some embodiments, one or more receivers may be located within the structure of the container. In some embodiments, the one or more receivers may be located on the exterior of the container. In some embodiments, the one or more receiver may be operably coupled to another device, such as for example one or more display devices, recording devices or transmission devices. For example, a receiver may be operably coupled to a display device on the exterior of the container so that when an appropriate signal is received, the display device indicates data, such as time or temperature data. For example, a receiver may be operably coupled to a transmission device so that when an appropriate signal is received, the transmission device transmits data, such as location, time, or positional data.

In some embodiments, there may be at least one region within an interior of a medicinal storage container such as those disclosed herein that is at a higher gaseous pressure than an atmospheric pressure external to the container. In some embodiments, there may be at least one compartment within one or more of the at least one medicinal storage region, wherein the at least one compartment is at a higher gaseous pressure than an exterior atmospheric pressure of the container. For example, in reference to FIGS. 6A and 6B, the gaseous pressure in a medicinal storage region 600, or within intermediate region 610, may be at a higher gaseous pressure than an atmospheric pressure external to the container. For example, a region of higher gaseous pressure may include a sealed region with inherently higher gaseous pressure. For example, a region of higher gaseous pressure may include at least one medicinal storage region including positive gaseous pressure relative to an atmospheric pressure external to the container. For example, a region of higher gaseous pressure may include at least one medicinal storage region including one or more sealed storage units with interior positive gaseous pressure relative to an atmospheric pressure external to the container. In some embodiments, there may be at least one region within the interior of the container that is at a lower atmospheric pressure than the atmospheric pressure external to the container. For example, in reference to FIGS. 6A and 6B, the gaseous pressure in a storage region 600, or within regions 610, may be at a lower gaseous pressure than an atmospheric pressure external to the container. For example, a region of lower gaseous pressure may include at least one medicinal storage region including negative gaseous pressure relative to an atmospheric pressure external to the container. For example, a region of lower gaseous pressure may include at least one medicinal storage region including one or more sealed storage units with interior negative gaseous pressure relative to an atmospheric pressure external to the container.

In some embodiments, a medicinal storage container may include at least one operable attachment to a medicinal dispensing device. For example, a medicinal storage container may include a region which may be attached to a needle-less or needle-free dispenser, including a needle-less injector, for selectable dispensation of a medicinal. For example, a medicinal storage container may include a region which may be attached to a liquid dispenser of oral dosages of a medicinal agent, for example a tube-like unit that allows for the flow of a medicinal liquid to a dispenser for appropriate dosage measure. For example, a medicinal storage container may include a region which may be attached to a liquid dispenser for intravenous administration of a medicinal, such as a tube-like unit that may be attached to an intravenous needle, pump or port. In some embodiments, a medicinal storage container may store multiple types of medicinal units and the container may include multiple operable attachments for various types of medicinal units, such as various tube-like attachments with various size and shape openings as appropriate for various medicinal units in different liquid, semi-solid, powder or gel-like forms.

Figure 2:
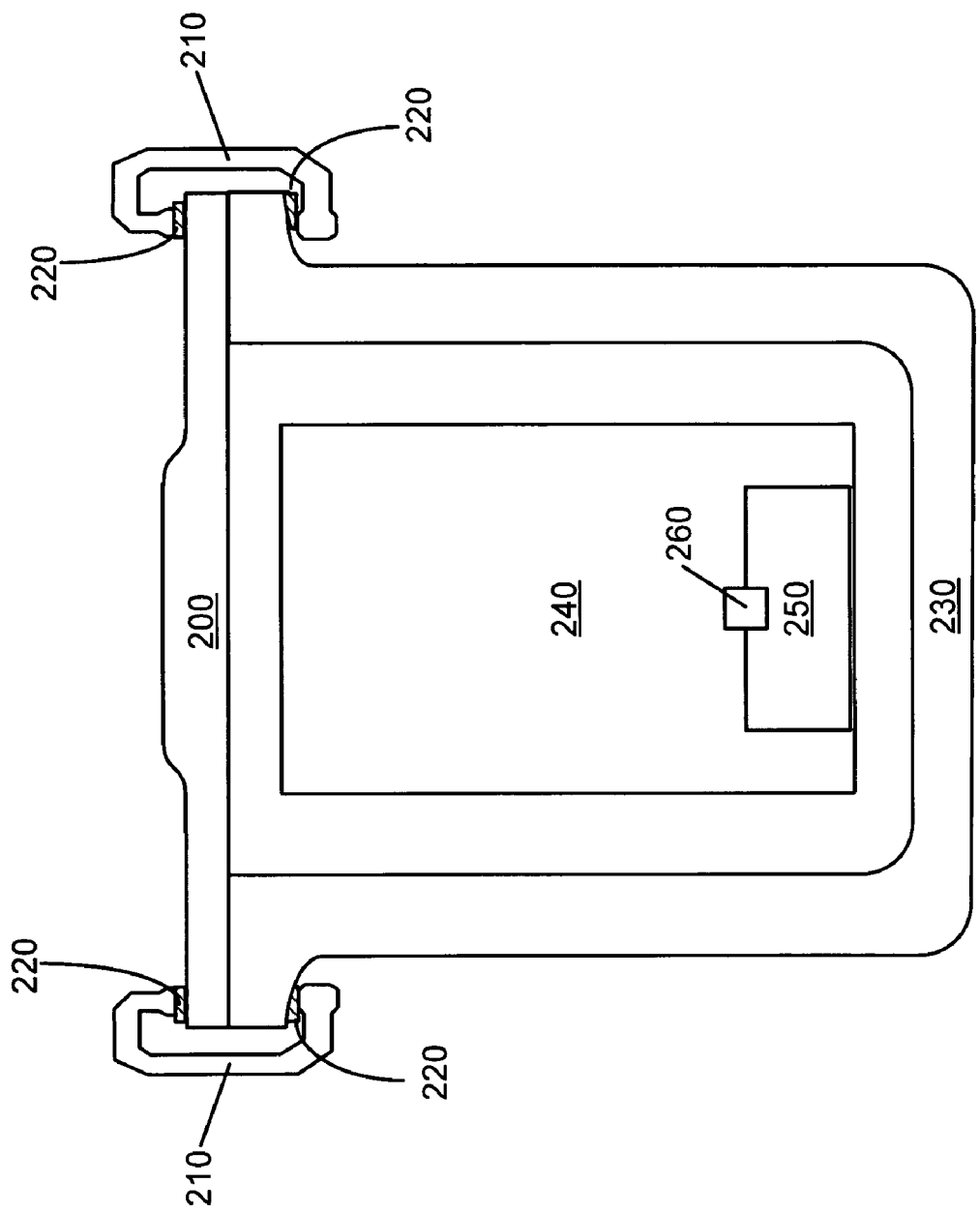
FIG. 2 is a schematic of some aspects of an integrally thermally sealed medicinal storage container.

With reference now to FIG. 2, shown is an example of an integrally thermally sealed medicinal storage container. As depicted in FIG. 2, an integrally thermally sealed medicinal storage container may include one or more segments of at least one ultra efficient insulation material 200, 230, the one or more segments principally defining at least one storage region, one or more regions of substantially thermally sealed connections 210, 220, between at least one of the one or more surface regions of the one or more segments wherein the one or more regions of substantially thermally sealed connections and the one or more segments form at least one integrally thermally sealed medicinal storage region 240, one or more thermal variant units 250, and at least one selectively-operable thermal conduction unit 260 between the at least one integrally thermally sealed medicinal storage region 240 and at least one of the one or more thermal variant units 250. Although the container depicted in FIG. 2 is illustrated in cross-section, it will be apparent that the one or more structural sections 210 and one or more sealing connection sections 220 form substantially thermally sealed connections around the circumference of the container or as needed in a specific embodiment to create substantially thermally sealed connections. Although the one or more regions of substantially thermally sealed connections depicted in FIG. 2 include multiple components, in some embodiments the one or more regions of substantially thermally sealed connections would include crimps, twists, welds or other structure to form one or more regions of substantially thermally sealed connections between one or more surface regions of the one or more segments of first ultra efficient insulation material 200, 230. The substantially thermally sealed connections may provide extremely low heat conductance and extremely low heat radiation transfer between integrally thermally sealed medicinal storage regions and the exterior of the container. The substantially thermally sealed connections may provide virtually zero heat conductance and virtually zero heat radiation transfer between substantially thermally sealed medicinal storage regions and the exterior of the container. In some embodiments, the substantially thermally sealed connections will allow less heat leak than the entire remainder of the container. In some embodiments, the substantially thermally sealed connections may double the heat seal relative to the remainder of the structure. For example, the heat leak through the substantially thermally sealed connections may be a factor of about 0.5 to a factor of about 2.0 relative to the heat leak through the remainder of the container. For example, the heat leak through the substantially thermally sealed connections may be a factor of about 0.1 to a factor of about 0.5 relative to the heat leak through the remainder of the container. The substantially thermally sealed connections may include any material or structure appropriate to the embodiment, for example: glues; adhesives; fasteners; welds; at least one layer of an ultra efficient insulation material; or at least one layer of a superinsulation material. Although the thermal variant unit 250 shown in FIG. 2 is enclosed within and adjacent to one side of the integrally thermally sealed medicinal storage region 240, in some embodiments one or more thermal variant units may be centrally located within an integrally thermally sealed medicinal storage region, separated from an integrally thermally sealed medicinal storage region, or there may be multiple thermal variant units.

Figure 3:
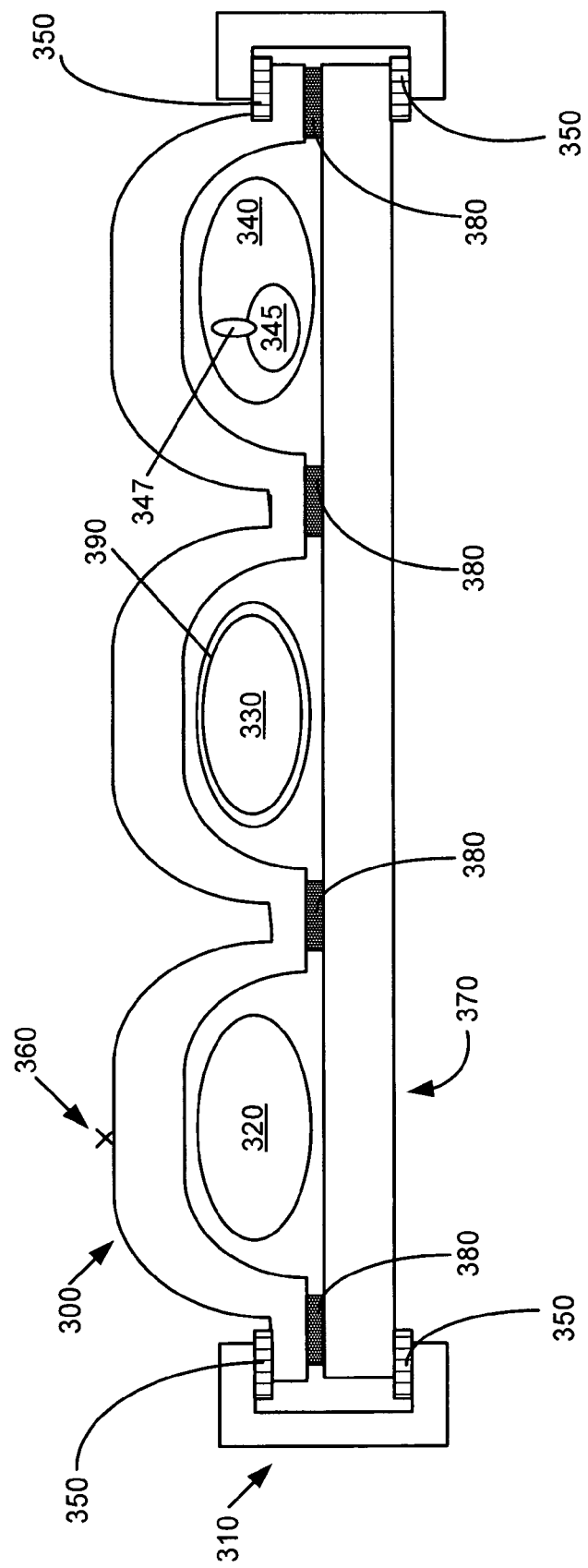
FIG. 3 is a schematic of some aspects of an integrally thermally sealed medicinal storage container.

With reference now to FIG. 3, shown is an example of an integrally thermally sealed medicinal storage container. As depicted in FIG. 3, an integrally thermally sealed medicinal storage container may include one or more segments of at least one ultra efficient insulation material 300, 370, the one or more segments principally defining at least one storage region, one or more regions of substantially thermally sealed connections 380, 350, between at least one of the one or more surface regions of the one or more segments wherein the one or more regions of substantially thermally sealed connections and the one or more segments form at least one integrally thermally sealed medicinal storage region 320, 330, 340, one or more thermal variant units 345, and at least one selectively-operable thermal conduction unit 347 between the at least one integrally thermally sealed medicinal storage region 320, 330, 340, and at least one of the one or more thermal variant units 345. Although the container depicted in FIG. 3 is illustrated in cross-section, it will be apparent that the one or more structural sections 300, 370 and one or more sealing connection sections 310 form substantially thermally sealed connections around the circumference of the container or as needed in a specific embodiment to create substantially thermally sealed connections. Although the one or more regions of substantially thermally sealed connections depicted in FIG. 3 include multiple components, in some embodiments the one or more regions of substantially thermally sealed connections would include crimps, twists, welds or other structure to form one or more regions of substantially thermally sealed connections between one or more surface regions of the one or more segments of ultra efficient insulation material 300, 370. In some embodiments, an integrally thermally sealed container may include at least one marking 360, for example at least one marking indicating a region where the container may be broken open to release stored material within one or more of the at least one integrally thermally sealed medicinal storage region. In some embodiments, an integrally thermally sealed medicinal storage container may include at least one layer of material including at least one metal on an interior surface of one or more of the at least one integrally thermally sealed medicinal storage region 390.

With reference now to FIG. 4, shown is an example of an integrally thermally sealed medicinal storage container. As depicted in FIG. 4, an integrally thermally sealed medicinal storage container may include one or more segments of at least one ultra efficient insulation material 300, 370, the one or more segments principally defining at least one storage region, one or more regions of substantially thermally sealed connections 380, 350, between at least one of the one or more surface regions of the one or more segments wherein the one or more regions of substantially thermally sealed connections and the one or more segments form at least one integrally thermally sealed medicinal storage region 320, 330, 340, one or more thermal variant units 345, and at least one selectively-operable thermal conduction unit 347 between the at least one integrally thermally sealed medicinal storage region 320, 330, 340, and at least one of the one or more thermal variant units 345. As depicted in FIG. 4, in some embodiments an integrally thermally sealed medicinal storage container may include one or more recording devices 400, 410, 420. As shown in FIG. 4, in some embodiments an integrally thermally sealed medicinal storage container may include one or more transmission devices 430, 440, 450. As illustrated in FIG. 4, in some embodiments an integrally thermally sealed medicinal storage container may include one or more display devices 460, 470. An integrally thermally sealed medicinal storage container system may include at least one remote display device 480.

With reference now to FIG. 5, shown is an example of an integrally thermally sealed medicinal storage container. As depicted in FIG. 5, an integrally thermally sealed medicinal storage container may include one or more segments of at least one ultra efficient insulation material 500, the one or more segments principally defining at least one storage region, one or more regions of substantially thermally sealed connections 505, between at least one of the one or more surface regions of the one or more segments wherein the one or more regions of substantially thermally sealed connections and the one or more segments form at least one integrally thermally sealed medicinal storage region 510, 515, 520, one or more thermal variant units 515, 529, and at least one selectively-operable thermal conduction unit 517, 527 between the at least one integrally thermally sealed medicinal storage region 510, 515, 520, and at least one of the one or more thermal variant units 515, 529. As shown in FIG. 5, some embodiments may include one or more temperature indicators 525, 530, 535. As depicted in FIG. 5, some embodiments may include one or more display devices 540, 545. An integrally thermally sealed medicinal storage container system may include at least one remote display device 575. As illustrated in FIG. 5, some embodiments may include one or more sensors 560, 555, 550. As depicted in FIG. 5, some embodiments may include at least one marking 565, such as a marking indicating a region where the container may be broken open to release stored material within one or more of the at least one thermally sealed medicinal storage region. As shown in FIG. 5, some embodiments include one or more heat sink units 580.

In some embodiments, an integrally thermally sealed medicinal storage container includes one or more heat sink units. In some embodiments, an integrally thermally sealed medicinal storage container includes one or more active cooling units. In some embodiments, an integrally thermally sealed medicinal storage container includes one or more regions of elevated thermal transfer within the container. An integrally thermally sealed medicinal storage container may include a plurality of substantially thermally sealed medicinal storage regions within the container. An integrally thermally sealed medicinal storage container may include one or more segments of at least one ultra efficient insulation material, wherein the ultra efficient insulation material includes at least one superinsulation material. An integrally thermally sealed medicinal storage container may include one or more segments of at least one ultra efficient insulation material, wherein the ultra efficient insulation material includes at least one multilayer insulation material. An integrally thermally sealed medicinal storage container may include one or more segments of at least one ultra efficient insulation material, wherein the ultra efficient insulation material includes at least two layers of thermal reflective material separated from each other by magnetic suspension. An integrally thermally sealed medicinal storage container may include one or more segments of at least one ultra efficient insulation material, wherein the ultra efficient insulation material includes at least one layer of thermal reflective material, and at least one spacer unit adjacent to the at least one layer of thermal reflective material.

An integrally thermally sealed medicinal storage container may include at least one selectively-operable thermal conduction unit, including at least one bimetallic unit. An integrally thermally sealed medicinal storage container may include at least one selectively-operable thermal conduction unit, including at least one mechanical actuator. An integrally thermally sealed medicinal storage container may include at least one selectively-operable thermal conduction unit, including at least one thermally-conductive fluid. An integrally thermally sealed medicinal storage container may include at least one controller operably coupled to one or more of the at least one selectively-operable thermal conduction units and at least one temperature sensor. The at least one controller may be an electronic controller, for example including one or more electronic switches, or triggers. The at least one controller may be a mechanical controller, for example a mechanical device that reversibly operates to exert mechanical force on one or more selectively-operable thermal conduction unit.

An integrally thermally sealed medicinal storage container may include one or more medicinal units within the integrally thermally sealed medicinal storage region, for example pills, capsules, syringes containing medicinals, unijets containing medicinals, vaccine vials, medicinal vials, patches or bandages, or packages containing any of these. In some embodiments, at least one of the one or more medicinal units is stored at a temperature between approximately 2° Centigrade and approximately 8° Centigrade. For example, some vaccine vials may have a suggested storage temperature between approximately 2° Centigrade and approximately 8° Centigrade. For example, one or more medicinal units may be stored between approximately 2° Centigrade and approximately 8° Centigrade to ensure maximum stability and efficacy of the stored medicinal material at the time of use or administration. One or more medicinal units may be stored at a temperature between approximately 2° Centigrade and approximately 8° Centigrade may include at least one of: at least one vaccine vial, at least one medicinal vial, at least one medicinal syringe, at least one needless injector, or at least one unijet.

An integrally thermally sealed medicinal storage container may include at least one layer of nontoxic material on an interior surface of the integrally thermally sealed medicinal storage region. An integrally thermally sealed medicinal storage container may include at least one layer of material including at least one metal on an interior surface of one or more of the at least one integrally thermally sealed medicinal storage region. The at least one metal on an interior surface of one or more of the at least one integrally thermally sealed medicinal storage region may include silver.

An integrally thermally sealed medicinal storage container may include at least one marking indicating a region where the container may be broken open to release stored material within the integrally thermally sealed medicinal storage region. For example, at least one marking may indicate a region where the container may be may be broken open, punctured or cracked to release stored material within one or more of the at least one substantially thermally sealed storage region. An integrally thermally sealed medicinal storage container may include one or more temperature indicators.

An integrally thermally sealed medicinal storage container may include one or more sensors. At least one of the one or more sensors may include a sensor of a gaseous pressure within one or more of the at least one storage region, a sensor of a mass within one or more of the at least one storage region, a sensor of a stored volume within one or more of the at least one storage region, a temperature sensor, or a sensor of an identity of an item within one or more of the at least one storage region. An integrally thermally sealed medicinal storage container may include one or more communications devices. The one or more communications devices may include at least one recording device, transmission device, display device or receiver. An integrally thermally sealed medicinal storage container may include at least one region within the container that is at a higher gaseous pressure than an atmospheric pressure exterior to the container.

Figure 6A:
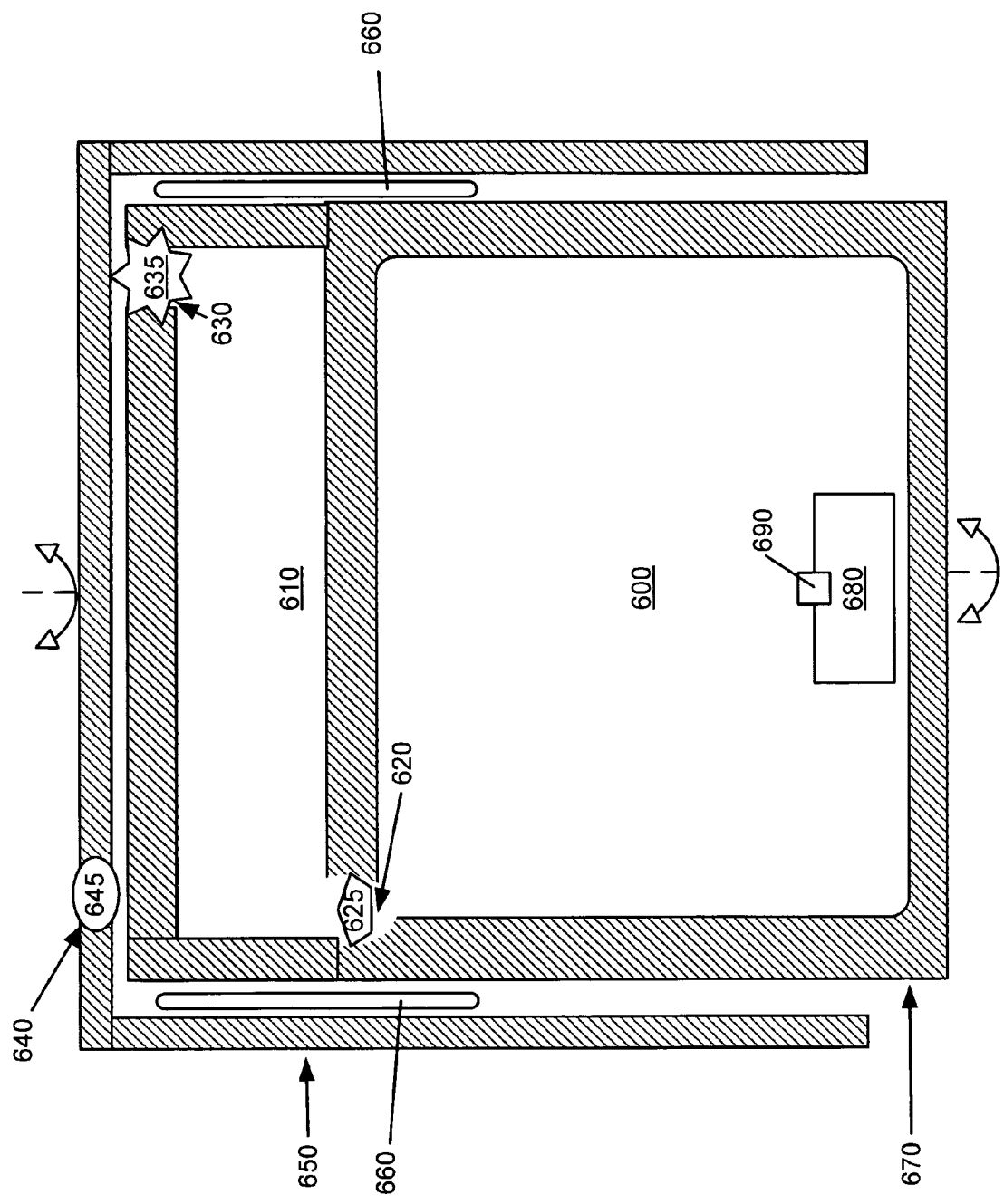
FIG. 6A is a schematic of some aspects of a temperature-stabilized medicinal storage container.
Figure 6B:
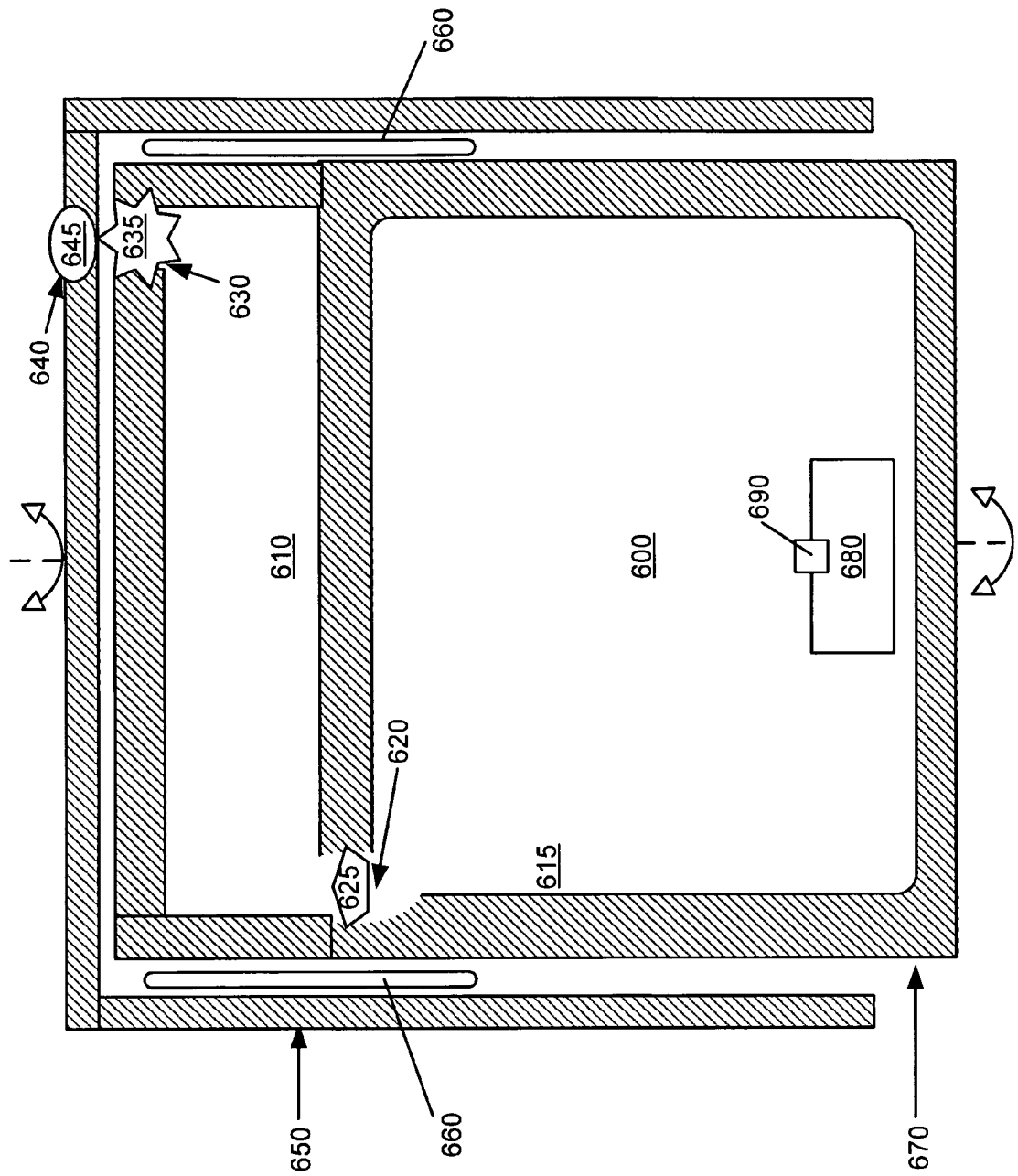
FIG. 6B is a schematic of some aspects of a temperature-stabilized medicinal storage container.

With reference now to FIGS. 6A and 6B, a temperature-stabilized medicinal storage container may include at least one medicinal storage structure, including one or more segments of at least one first ultra efficient insulation material 670 shaped to define at least one substantially temperature-stabilized medicinal storage region 600, one or more thermal variant units 680, and at least one selectively-operable thermal conduction unit 690 between one or more of the at least one substantially temperature-stabilized medicinal storage region 600 and at least one of the one or more thermal variant units 680, and at least one access structure, including at least one conduit 630, 640 connecting the at least one substantially temperature-stabilized medicinal storage region 600 and at least one external region of the container, at least one segment of first thermal conduction barrier material surrounding the region of the at least one conduit that connects to the at least one external region of the container, and at least one cover 650 including at least one segment of second thermal conduction barrier material substantially conforming to the at least one segment of first thermal conduction barrier material, wherein the at least one cover includes at least one second ultra efficient insulation material. At least one conduit 620 may connect one or more intermediate regions 610 and at least one substantially temperature-stabilized medicinal storage region 600. As shown in FIGS. 6A and 6B, there may be one or more selectively-operable closures 625, 635, 645 operably-coupled to one or more conduits 620, 630, 640. As depicted in FIGS. 6A and 6B, a temperature-stabilized medicinal storage container may include at least one cover 650 which may rotate through a thermally sealed rotation region 660. For example a thermally sealed rotation region 660 may include hinges, curves or grooves to allow for movement of at least one cover 650 around an axis of the at least one medicinal storage region 600. As depicted in FIG. 6B, when the at least one cover 650 is in a position to allow for alignment of conduit 640 with conduit 630, at least one passageway may be formed between at least one substantially temperature-stabilized medicinal storage region 600 and the exterior of the container via intermediate region 610. As depicted in FIG. 6A, at least one cover 650 also may be in a position to not allow alignment of conduit 640 with conduit 630. The at least one cover 650 may therefore include an externally-operable closure operably coupled to one or more of the at least one second selectively operable passageway. As may be readily apparent from FIGS. 6A and 6B, material stored in the medicinal storage region may include liquids, fluids, semi-fluids, solids, semi-solids, particulates, or medicinal storage units (e.g. one or more packaged medicinal units).

Figure 7:
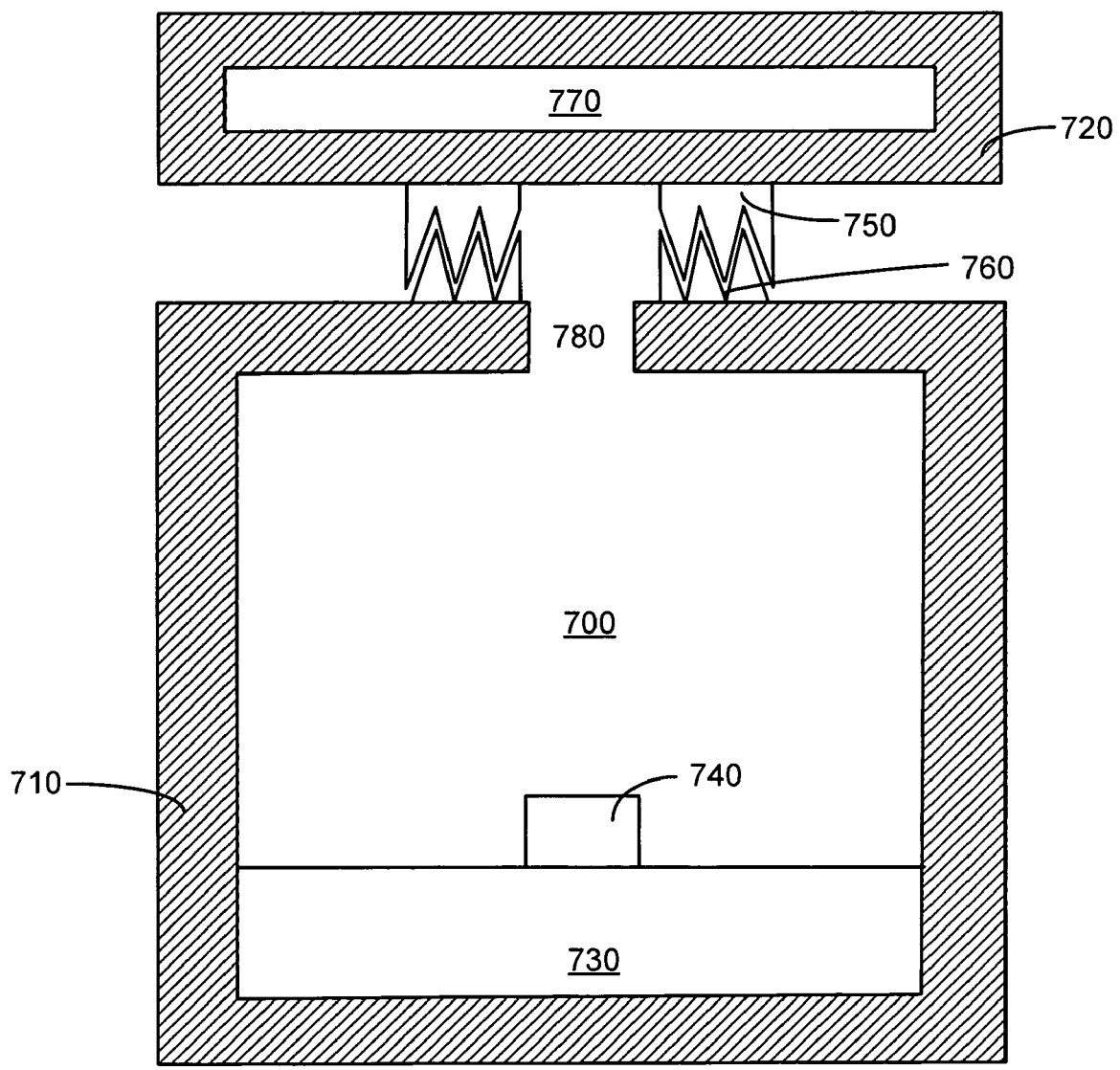
FIG. 7 is a schematic of some aspects of a temperature-stabilized medicinal storage container.

With reference now to FIG. 7, a temperature-stabilized medicinal storage container may include at least one medicinal storage structure, including one or more segments of at least one first ultra efficient insulation material 710 shaped to define at least one substantially temperature-stabilized medicinal storage region 700, one or more thermal variant units 730, and at least one selectively-operable thermal conduction unit 740 between one or more of the at least one substantially temperature-stabilized medicinal storage region 700 and at least one of the one or more thermal variant units 730, and at least one access structure, including at least one conduit 780 connecting the at least one substantially temperature-stabilized medicinal storage region 700 and at least one external region of the container, at least one segment of first thermal conduction barrier material 750 surrounding the region of the at least one conduit that connects to the at least one external region of the container, and at least one cover 720 including at least one segment of second thermal conduction barrier material 760 substantially conforming to the at least one segment of first thermal conduction barrier material, wherein the at least one cover includes at least one second ultra efficient insulation material. In some embodiments, the at least one conduit 780 may be substantially defined by one or more segments of the first ultra efficient insulation material. In some embodiments, the at least one cover may include at least one heat sink 770 and at least one selectively-operable thermal conduction unit, which may, for example, be operably-coupled to the at least one conduit.

Figure 8:
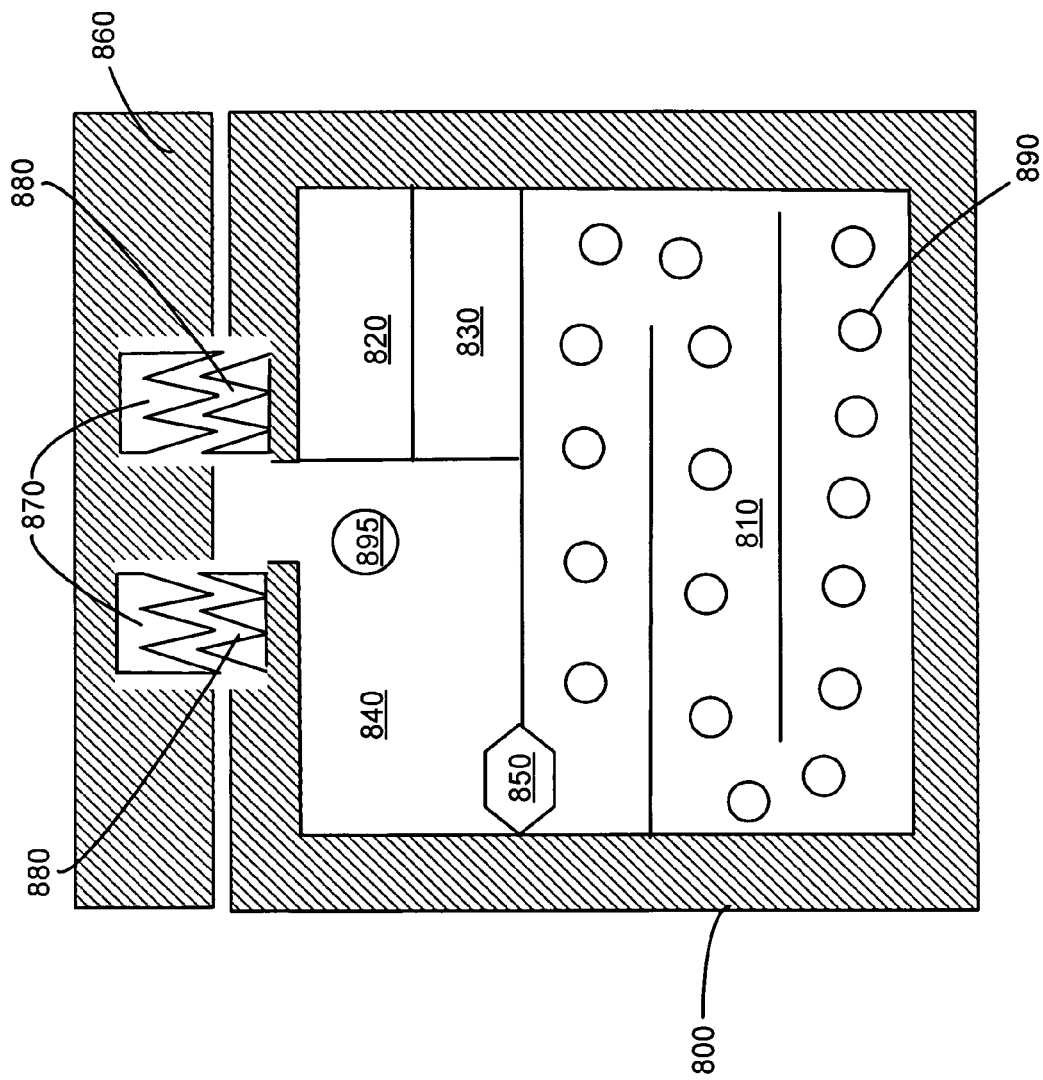
FIG. 8 is a schematic of some aspects of a temperature-stabilized medicinal storage container.

With reference now to FIG. 8, a temperature-stabilized medicinal storage container may include at least one medicinal storage structure, including one or more segments of at least one first ultra efficient insulation material 800 shaped to define at least one substantially temperature-stabilized medicinal storage region 810, one or more thermal variant units 820, and at least one selectively-operable thermal conduction unit 830 between one or more of the at least one substantially temperature-stabilized medicinal storage region 810 and at least one of the one or more thermal variant units 820, and at least one access structure, including at least one conduit 840 connecting the at least one substantially temperature-stabilized medicinal storage region 810 and at least one external region of the container, at least one segment of first thermal conduction barrier material 880 surrounding the region of the at least one conduit that connects to the at least one external region of the container, and at least one cover 860 including at least one segment of second thermal conduction barrier material 870 substantially conforming to the at least one segment of first thermal conduction barrier material, wherein the at least one cover includes at least one second ultra efficient insulation material. A substantially temperature-stabilized medicinal storage region 810 may include multiple medicinal units 890, configured, for example, by shape, contents, maximum storage capacity, or accessibility. In some embodiments, a medicinal storage container includes inner assembly including one or more interlocks configured to provide controllable egress of a quantity of a material from one or more of the at least one thermally sealed medicinal storage region. For example, FIG. 8 shows a substantially thermally sealed container including an interlock 850 configured to provide controllable egress of medicinal units 890 from substantially temperature-stabilized medicinal storage region 810 into conduit 840. For example, FIG. 8 depicts medicinal unit 895 within conduit 840.

In some embodiments, the first thermal conduction barrier material includes one or more metal alloy, such as one or more titanium alloy. A titanium alloy may include an alpha-beta ($\alpha$-$\beta$) titanium alloy, such as Ti-6% Al-4% V alloy. In some embodiments, the first thermal conduction barrier material and the second thermal conduction barrier material are substantially the same. In some embodiments, the at least one segments of first thermal conduction barrier material and the at least one segment of second thermal conduction barrier material include more than one pleat structure, and wherein the pleat structures from the at least one segments of first thermal conduction barrier material and the at least one segments of second thermal conduction barrier material are shaped to interleave with each other. For example, FIG. 7 depicts first thermal conduction barrier material 760 interleaving with second thermal conduction barrier material 750. For example, FIG. 8 depicts first thermal conduction barrier material 880 interleaving with second thermal conduction barrier material 870. Although FIGS. 7 and 8 depict containers in a 2-dimensional cross-section, materials shaped to interleave with each other may surround or encircle the conduit in a 3-dimensional view.

Figure 9B:
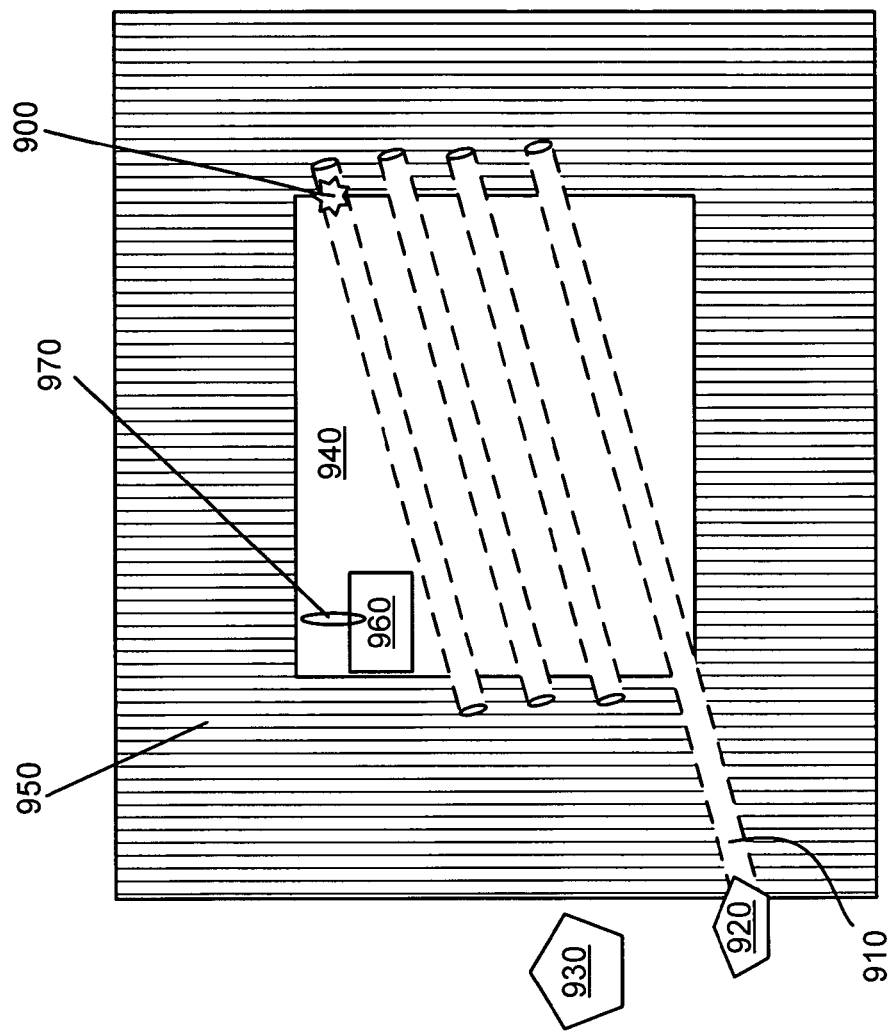
FIG. 9B is a schematic of some aspects of a temperature-stabilized medicinal storage container.
Figure 9A:
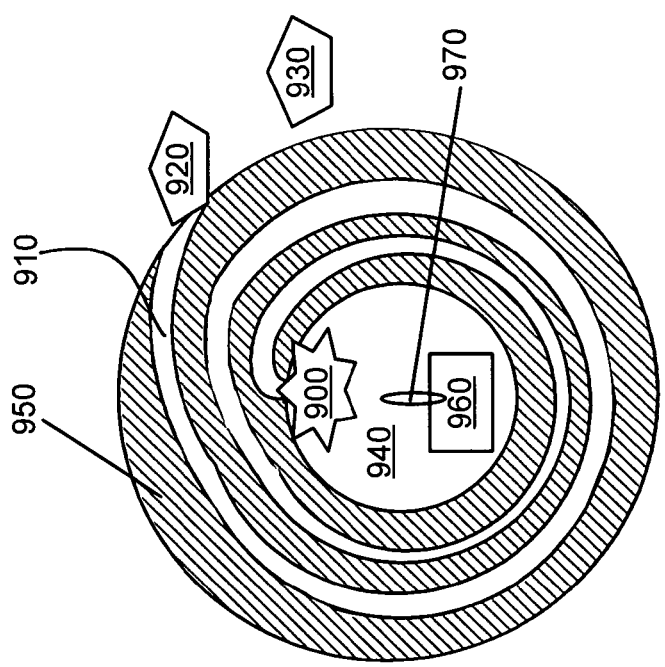
FIG. 9A is a schematic of some aspects of a temperature-stabilized medicinal storage container.
Figure 9C:
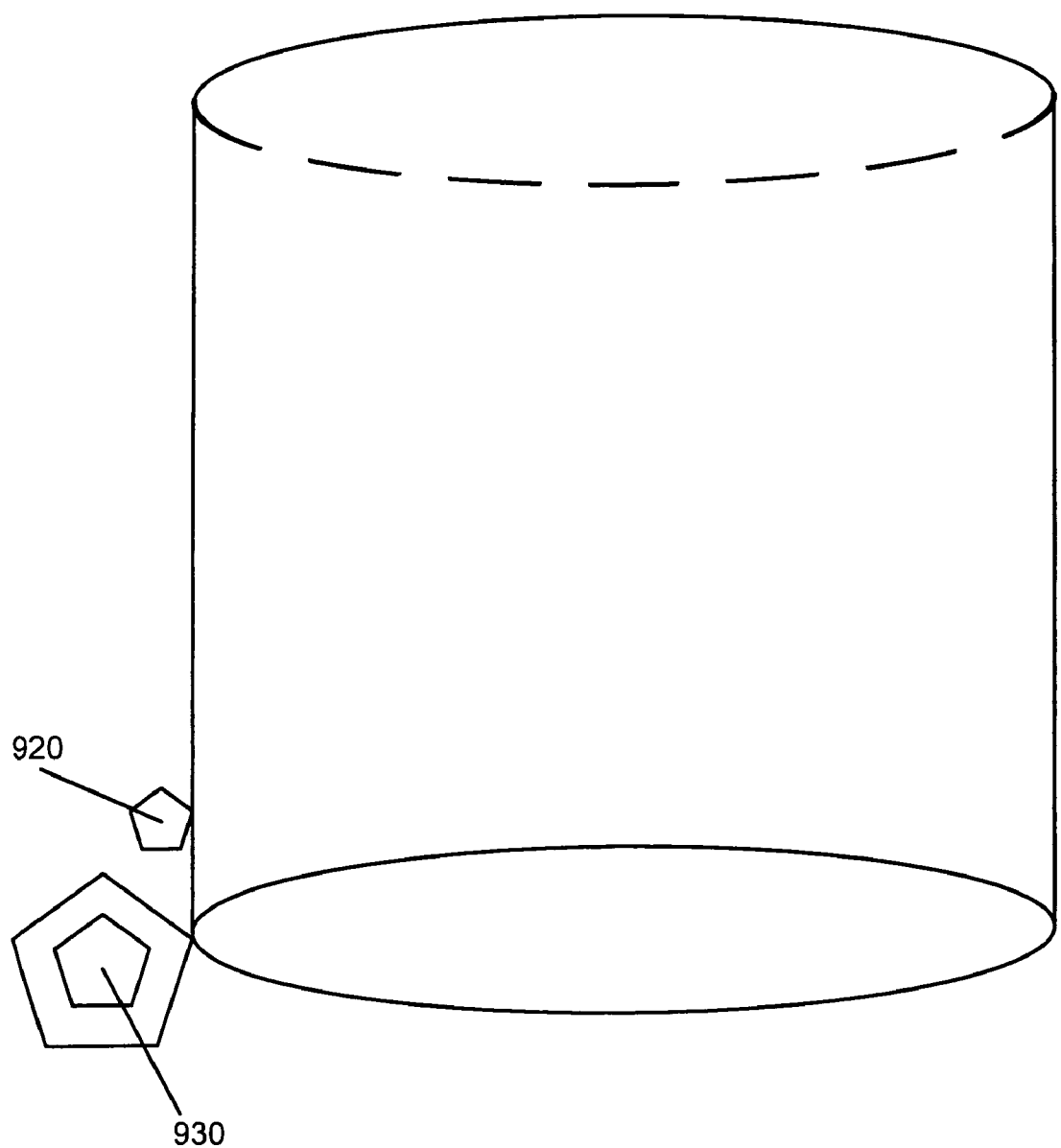
FIG. 9C is a schematic of some aspects of a temperature-stabilized medicinal storage container.

With reference to FIGS. 9A, 9B and 9C, in some embodiments a temperature-stabilized medicinal storage container includes a structural assembly including one or more sections of ultra efficient insulation material 950 primarily defining at least one substantially thermally sealed medicinal storage region 940, an outlet assembly including one or more outlet channels 910, wherein the one or more outlet channels are arranged to provide controllable egress of a quantity of a stored material from the at least one substantially thermally sealed medicinal storage region 940, and the one or more outlet channels substantially follow an extended thermal pathway, one or more thermal variant units 960, and at least one selectively-operable thermal conduction unit 970 between one or more of the at least one substantially temperature-stabilized medicinal storage region 940 and at least one of the one or more thermal variant units 960. For example, an extended thermal pathway may have a high aspect ratio. For example, as illustrated in FIGS. 9A, 9B and 9C, a substantially thermally sealed container includes an outlet channel 910 to provide controllable egress of a quantity of a stored material from the at least one medicinal storage region 940. View 9A depicts a top-down cross-section view of a medicinal storage container, view 9B depicts a side-facing cross-section view of the container, and view 9C depicts an external side-facing view of the container. In some embodiments, a medicinal storage container includes inner assembly including one or more interlocks configured to provide controllable egress of a quantity of a material from one or more of the at least one thermally sealed medicinal storage region. For example, FIG. 9 shows a substantially thermally sealed container including an outlet channel 910 and an interlock 900 between the outlet channel and the at least one thermally sealed medicinal storage region 940. In some embodiments, a medicinal storage container includes at least one externally-controllable opening between at least one of the one or more outlet channels and the exterior of the container. For example, FIG. 9 shows a medicinal storage container including an outlet channel 910 and an externally-controllable opening 920 between the outlet channel and the exterior of the container. A medicinal storage container may include a sealable cover 930 for an externally-controllable opening 920. A sealable cover for an externally-controllable opening may include a thermally sealable cover, and may include at least one ultra efficient insulation material.

Figure 10:
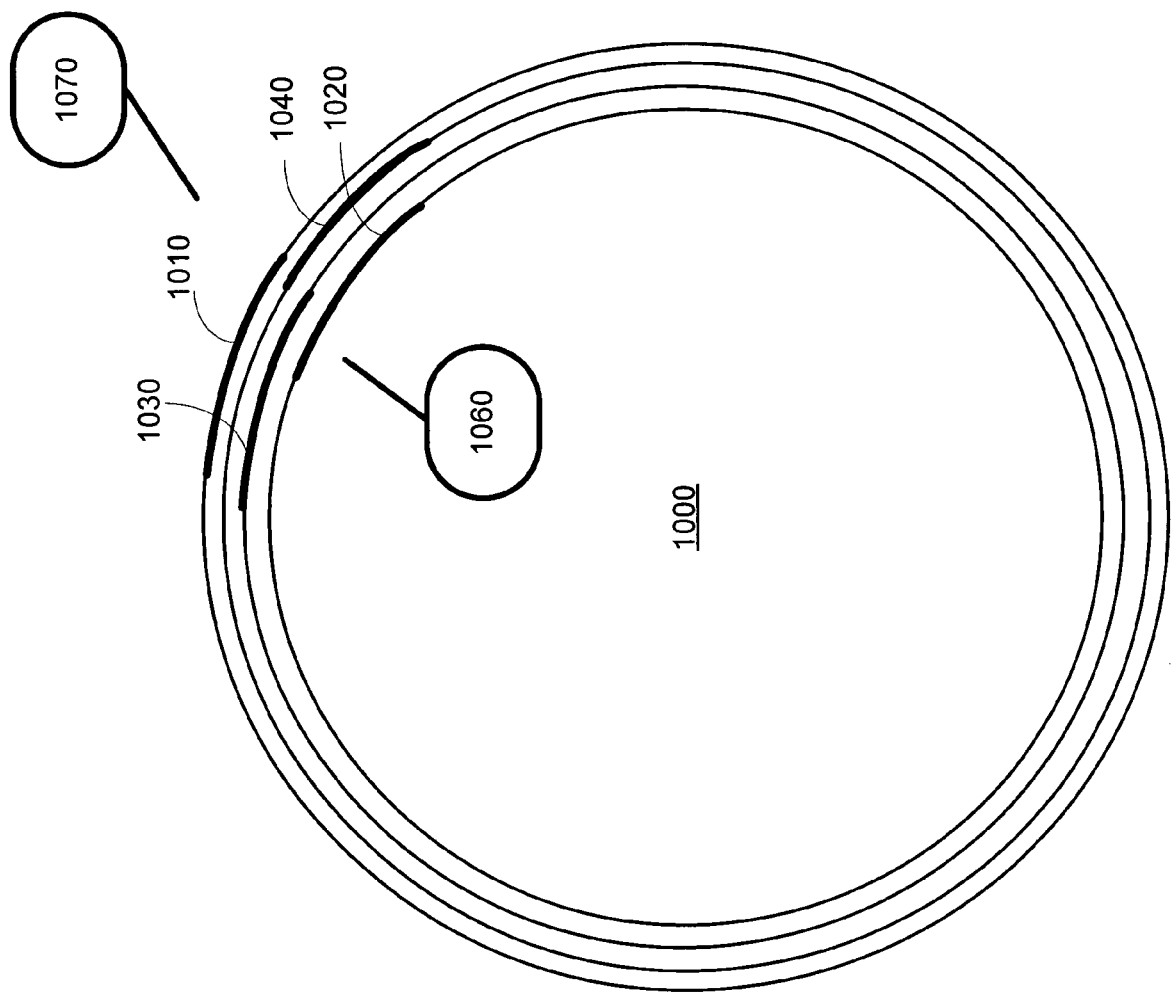
FIG. 10 is a schematic of some aspects of a temperature-stabilized medicinal storage container.
Figure 11:
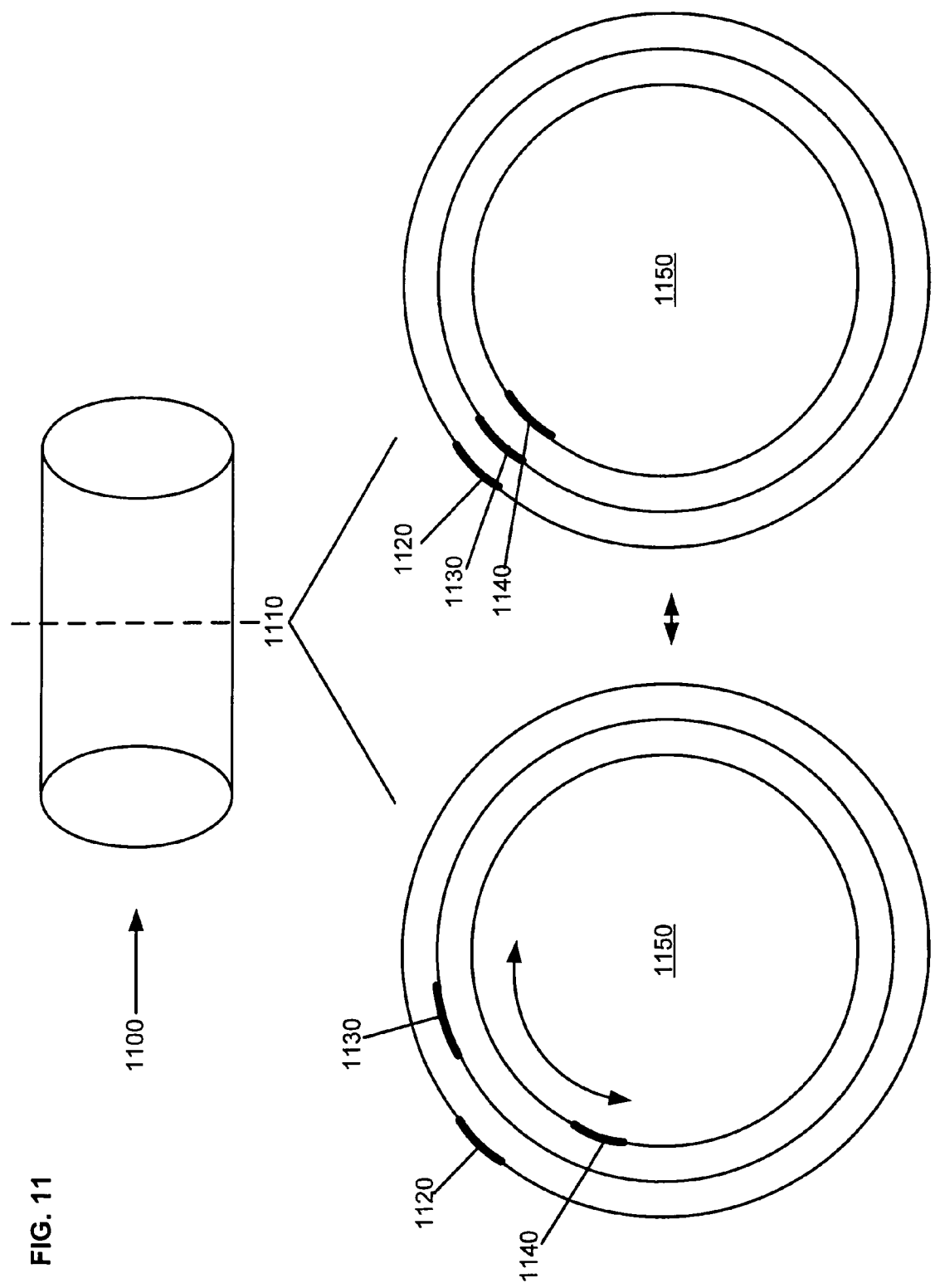
FIG. 11 is a schematic of some aspects of a temperature-stabilized medicinal storage container.

In some embodiments, a temperature-stabilized medicinal storage container may include at least one medicinal storage structure, including one or more segments of at least one ultra efficient insulation material shaped to define at least one substantially temperature-stabilized medicinal storage region, one or more thermal variant units, and at least one selectively-operable thermal conduction unit between one or more of the at least one substantially temperature-stabilized medicinal storage region and at least one of the one or more thermal variant units, at least one access region, including at least one region of the one or more segments of an ultra efficient insulation material configured for at least one perforation by at least one perforation device, wherein one or more of the at least one perforation is configured to provide for a controlled egress of a quantity of a medicinal material from the at least one substantially temperature-stabilized medicinal storage region. For example, FIGS. 10 and 11 depict that an access region may include multiple regions 1040, 1030, 1120, 1130, 1140, of one or more segments of an ultra efficient insulation material configured for at least one perforation by a perforation device. Some embodiments may include a container with at least one exterior wall and at least one interior wall wherein one or more of the at least one exterior wall and one or more of the at least one interior wall are movable relative to each other, and the relative movement of the exterior wall to the interior wall alters the accessibility of one or more of the at least one region of the one or more segments of an ultra efficient insulation material configured for at least one perforation by a perforation device. For example, FIG. 10 depicts an exterior wall 1010 and an interior wall 1020 which may be movable relative to each other. In some embodiments, the relative movement of the at least one exterior wall and the at least one interior wall may facilitate access to the at least one storage region. For example, in FIG. 10, the relative movement of an exterior wall 1010 and an interior wall 1020 may allow the alignment of an access region, including at least one region of one or more segments of ultra-efficient insulation material configured for at least one perforation by a perforation device. In some embodiments, layers of ultra efficient insulation material may be movable relative to each other to facilitate access to the at least one medicinal storage region. For example, FIG. 11 depicts layers of ultra efficient insulation material 1120, 1130 and 1140 which are movable relative to each other along axis of rotation 1110 of the container 1100 to align and facilitate access to medicinal storage region 1150.

Some embodiments may include wherein the at least one access region includes at least one substantially tubular structure, wherein the at least one substantially tubular structure is of a size and shape to provide for controlled egress of a discrete quantity of a medicinal material from the at least one substantially temperature-stabilized medicinal storage region. A substantially tubular structure may include a tube made of a variety of materials appropriate to the embodiment, or a tube-like structure made of a variety of materials appropriate to the embodiment. In some embodiments, the at least one substantially tubular structure includes at least one hypodermic syringe. In some embodiments, one or more of the at least one substantially tubular structure are located external to the container, and may be transiently inserted from the exterior of the container to the interior of the container to provide for the controlled egress of a discrete quantity of a substance from the at least one storage region. For example, FIG. 10 depicts a movable perforation device with a substantially tubular structure 1070 located external to the container, wherein substantially tubular structure 1070 is positioned for piercing at least one region of the one or more segments of an ultra efficient insulation material configured for at least one perforation by a perforation device. In some embodiments, the one or more of the at least one substantially tubular structure are located internal to the container, and may be transiently inserted from the interior of the container to the exterior of the container to provide for the controlled egress of a discrete quantity of a substance from the at least one storage region. For example, FIG. 10 depicts a movable perforation device with a substantially tubular structure 1060 located within medicinal storage region 1000, wherein substantially tubular structure 1070 is positioned for piercing at least one region of the one or more segments of an ultra efficient insulation material configured for at least one perforation by a perforation device. There may be a plurality of movable perforation devices with at least one substantially tubular structure stored within or external to the storage structure. At least one substantially tubular structure may be replaceable.

Figure 12:
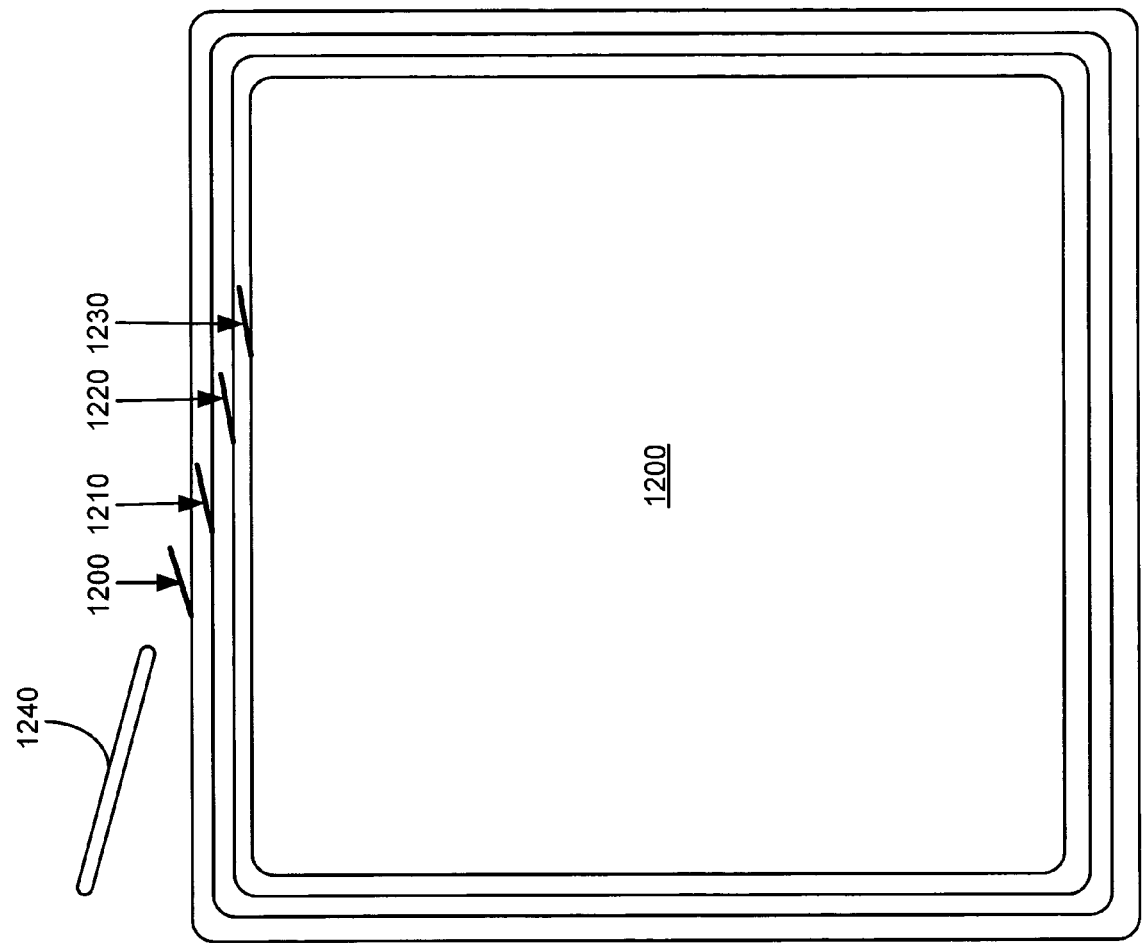
FIG. 12 is a schematic of some aspects of a temperature-stabilized medicinal storage container.

Some embodiments of a medicinal storage container may include an access region, including at least one region of the one or more segments of an ultra efficient insulation material configured for at least one perforation by at least one perforation device, wherein one or more of the at least one perforation is configured to provide for a controlled egress of a quantity of a medicinal material from the at least one substantially temperature-stabilized medicinal storage region. For example, FIG. 12 depicts regions 1200, 1210, 1220, 1230 of one or more segments of an ultra efficient insulation material which may be perforated to allow for the transient insertion of perforation device 1240 from the exterior of the container to the interior of the at least one substantially temperature-stabilized medicinal storage region 1200. As depicted in FIG. 12, in some embodiments one or more of the at least one region of the one or more segments of an ultra efficient insulation material configured for at least one perforation by at least one perforation device may be configured to permit perforation at a specific angle, direction, or range.

In some embodiments, a temperature-stabilized medicinal storage container may include an access region, which may include an elongated thermal pathway. For example, the elongated thermal pathway may be a pathway for the controlled egress of a quantity of a medicinal material, including at least one medicinal unit, from the at least one substantially temperature-stabilized storage region. For example, the at least one access region including an elongated thermal pathway may be configured to include a high aspect ratio. In some embodiments, a temperature-stabilized medicinal storage container may include an access region, which may include at least one substantially tubular structure, wherein the at least one substantially tubular structure is of a size and shape to provide for a controlled egress of a quantity of a medicinal material from the at least one substantially temperature-stabilized medicinal storage region. For example, at least one substantially tubular structure may include a tube of an appropriate size and shape to dispense a liquid medicinal material at a fixed rate. For example, at least one substantially tubular structure may include at least one hypodermic syringe. For example, at least one substantially tubular structure may include a tubular structure of the correct size and shape to provide for controlled egress of a particular variety of medicinal vials, such as vaccine vials.

In some embodiments, a temperature-stabilized medicinal storage container may include a plurality of medicinal storage structures. For example, a temperature-stabilized medicinal storage container may include more than one substantially temperature-stabilized medicinal storage regions. A temperature-stabilized medicinal storage container may include one or more inserts to segregate, hold, insulate, or protect one or more medicinal units. In some embodiments, a temperature-stabilized medicinal storage container may include one or more heat sink units. In some embodiments, a temperature-stabilized medicinal storage container may include one or more active cooling units. In some embodiments, one or more thermal variant units may include one or more regions of elevated thermal transfer within the container. In some embodiments, one or more of the at least one selectively-operable thermal conduction units may include: at least one bimetallic unit, at least one mechanical actuator, or at least one thermally-conductive fluid. In some embodiments, a temperature-stabilized medicinal storage container may include at least one controller operably coupled to one or more of the at least one selectively-operable thermal conduction units and at least one temperature sensor. One or more of the at least one controller may be an electronic controller, or a mechanical controller. In some embodiments, a temperature-stabilized medicinal storage container may include at least one first ultra efficient insulation material, which may include at least one superinsulation material, at least one multilayer insulation material, or at least two layers of thermal reflective material separated from each other by magnetic suspension. In some embodiments, a temperature-stabilized medicinal storage container may include at least one first ultra efficient insulation material, which may include at least one layer of thermal reflective material, and at least one spacer unit adjacent to the at least one layer of thermal reflective material. In some embodiments, the first ultra efficient insulation material and the second ultra efficient insulation material are substantially the same, while in other embodiments the first ultra efficient insulation material and the second ultra efficient insulation material may not be substantially the same.

In some embodiments, a temperature-stabilized medicinal storage container may include a plurality of substantially temperature-stabilized medicinal storage regions. For example, a container may include a plurality of medicinal storage structures, or a plurality of substantially temperature-stabilized storage regions within one or more medicinal storage structures. In some embodiments, a temperature-stabilized medicinal storage container may include at least one layer of nontoxic material on an interior surface of one or more of the at least one substantially temperature-stabilized medicinal storage region. In some embodiments, a temperature-stabilized medicinal storage container may include at least one layer of material including at least one metal on an interior surface of one or more of the at least one substantially temperature-stabilized medicinal storage region. For example, the at least one layer of material including at least one metal may include silver.

In some embodiments, a temperature-stabilized medicinal storage container may include embodiments where the at least one conduit is substantially defined by one or more segments of the first ultra efficient insulation material. In some embodiments, a temperature-stabilized medicinal storage container may include embodiments wherein a first thermal conduction barrier material includes at least one alloy. For example, a first thermal conduction barrier material may include one or more titanium alloy. In some embodiments, the first thermal conduction barrier material and the second thermal conduction barrier material are substantially the same, while in other embodiments the first thermal conduction barrier material and the second thermal conduction barrier material are not substantially the same. In some embodiments, the at least one segment of first thermal conduction barrier material and the at least one segment of second thermal conduction barrier material include more than one pleat structure, and wherein the pleat structures from the at least one segment of first thermal conduction barrier material and the at least one segment of second thermal conduction barrier material are shaped to interleave with each other.

In some embodiments, a temperature-stabilized medicinal storage container may include one or more temperature indicators. In some embodiments, a temperature-stabilized medicinal storage container may include one or more sensors. At least one of the one or more sensors may include: sensor of a gaseous pressure within one or more of the at least one storage region, sensor of a mass within one or more of the at least one storage region, sensor of a stored volume within one or more of the at least one storage region, temperature sensor, or sensor of an identity of an item within one or more of the at least one storage region. In some embodiments, a temperature-stabilized medicinal storage container may include one or more communications devices. At least one of the one or more communications devices may include: one or more recording devices, one or more transmission devices, one or more display devices, or one or more receivers. For example, one or more display devices may be within one or more storage region, connected to an external region of the container, or located at a distance from the container.

In some embodiments, a temperature-stabilized medicinal storage container may include at least one area within the container that is at a higher gaseous pressure than an atmospheric pressure external to the container. In some embodiments, a temperature-stabilized medicinal storage container may include at least one area within the container that is at a lower gaseous pressure than an atmospheric pressure external to the container.

In some embodiments, a temperature-stabilized medicinal storage container may include one or more transport devices attached to the container. For example, one or more transport devices may include one or more straps, handles, or slings. In some embodiments, one or more temperature-stabilized medicinal storage containers may be connected to, or secured within, a backpack-like transport device. In some embodiments, one or more transport devices may include one or more grips, ring-like structures, or mating connections to a carrier or lifting device. For example, a temperature-stabilized medicinal storage container may include metal rings attached to the outside of the container at intervals appropriate for use in lifting the container with a dolly, handcart, hand-truck, or forklift.

In some embodiments, a medicinal storage container includes at least one marking on the exterior of the container indicating at least one access region. For example, at least one marking may include ink, paint, UV-visible markings, coded markings, tell-tale marks or structural marks on the exterior of the container (e.g. indentations or scratch marks). In some embodiments, a medicinal storage container includes a framework attached to an exterior of the container identifying one or more of the at least one region of one or more segments of an ultra efficient insulation material configured for at least one perforation by a perforation device. For example, a framework may include an access structure or provide an appropriate alignment for perforation by a perforation device.

In some embodiments, a medicinal storage container includes at least one authentication device. An authentication device may be operably coupled to one or more communications devices, sensors, or access mechanisms. For example, an authentication device may include a device which may be authenticated with a key, or a device that may be authenticated with a code, such as a password or a combination. For example, an authentication device may include a device that may be authenticated using biometric parameters, such as fingerprints, retinal scans, hand spacing, voice recognition or biofluid composition (e.g. blood, sweat, or saliva).

In some embodiments, a medicinal storage container includes at least one logging device. A logging device may be operably coupled to one or more communications devices, sensors, perforation devices or access mechanisms. For example, a logging device may include a record of authentication via an authentication device, such as a record of times of authentication, operation of authentication or individuals making the authentication. For example, a logging device may record that an authentication device was authenticated with a specific code which identifies a specific individual at one or more specific times. For example, a logging device may record egress of a quantity of a material from one or more of at least one storage region, such as recording that some quantity or units of material egressed at a specific time. For example, a logging device may record information from one or more sensors, one or more temperature indicators, or one or more communications devices.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired. Furthermore, the use of particular shapes within a Figure herein is not intended to connote a shape of any particular element. For example, the use of a star-shape for element 400 in FIG. 4 should not be interpreted as meaning that the element 400 in practice should be star-shaped.

All of the above U.S. patents, U.S. patent application publications, U.S. patent applications, foreign patents, foreign patent applications and non-patent publications referred to in this specification or listed in any Application Data Sheet, are incorporated herein by reference, to the extent not inconsistent herewith.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). It will be further understood by those within the art that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

EXAMPLES

Example 1

A medicinal storage container may be used to maintain a vaccine at an optimal storage temperature. The optimal storage temperature for many vaccines including those for tuberculosis, diphtheria, tetanus, pertussis, hepatitis, influenza, measles, mumps, rubella, and polio, for example, ranges from 2 to 8° C. (Center for Disease Control/Department of Health & Human Services, Vaccine Management: Recommendations for storage and handling of selected biologicals (January 2007), which is herein incorporated by reference). A vaccine may lose potency upon exposure to inappropriate temperature conditions and the loss in vaccine potency is dependent, for example, upon whether an adjuvant is present, whether the vaccine is live or inactivated and whether the vaccine is liquid or lyophilized (Pickering et al., Too hot, too cold: Issues with vaccine storage, Pediatrics 118:1738-1739 (2006), which is herein incorporated by reference). For example, live attenuated vaccines are stable at freezing temperatures but lose potency after exposure to temperatures above the recommended range. In contrast, vaccines containing aluminum adjuvants irreversibly lose potency when exposed to freezing temperatures. Maintaining a vaccine at a constant temperature between 2 to 8° C. from the time it is manufactured to the time it is administered to a patient poses a challenge for both industrialized as well as developing countries. In one study, for example, 20% of physician offices or health care facilities in Ontario, Canada did not meet the necessary requirements for vaccine storage and handling, including having refrigerators that were either too hot or too cold for safe vaccine storage and leaving vaccines out of the refrigerator for too long (Weir & Hatch, Preventing cold chain failure: vaccine storage and handling, JAMC 171:1050 (2004), which is herein incorporated by reference). In a developing or resource-limited country or region, the challenges are even greater with potentially limited refrigeration and often extreme heat and humidity.

Example 2

A medicinal storage container may be used to maintain a vaccine at a temperature of 2 to 8° C. for use in an industrialized, developing or resource-limited country or region. For example, the World Health Organization (WHO) currently recommends the following vaccinations for children from birth to nine months of age: BCG (tuberculosis), oral polio (in endemic countries), diphtheria-tetanus-pertussis, hepatitis B, *Haemophilus influenzae* type B, yellow fever (where this disease poses a threat), and measles (Disease Control Priorities Project). As such, a single dose of a vaccine may be stored in an integrally sealed medicinal storage container and may be packaged, for example, in a preloaded, single-use syringe, a vial, or a single-dose injection device such as, for example, the Uniject (see, e.g. Levin et al., The costs of home delivery of a birth dose of hepatitis B vaccine in a prefilled syringe in Indonesia, Bull. World Health Org. 83:456-461 (2005), which is herein incorporated by reference). Alternatively, multiple doses of a vaccine may be enclosed in an integrally sealed medicinal storage container for use by multiple individuals on a given day. As such, the vaccine may be packaged as single dose units, as described above or as multi-dose units in, for example, a multi-dose vial. A medicinal storage container may contain only a single type of vaccine. Alternatively, a medicinal storage container may contain multiple vaccines intended to be administered all at once, for example, to a child of a particular age. Optionally, multiple single or multi-dose units of a vaccine or vaccines may be enclosed in a medicinal storage container and as such a single unit or multiple units may be dispensed over time without compromising the temperature stability of the remaining units. In some instances, single or multiple doses of a vaccine may be directly packaged in a medicinal storage container and accessed via an access region of the container.

Example 3

A medicinal storage container may be used to maintain oral medications such as, for example, tablets or capsules at an optimal temperature. The shelf-life or expiration date of a medication is based on specified storage requirements. While temperate climate conditions generally satisfy these requirements, the potentially extreme heat and humidity of tropical climates in resource-limited areas lacking appropriate storage capability may significantly increase the rate of drug decomposition and consequently decrease the expected shelf-life. For example, three month exposure of tablets and capsules of the antibiotics sulphathathiazole, tetracycline hydrochloride, and chloramphenicol to a temperature of 30° C. and relative humidity of 75% decreases the shelf-lives of these drugs from 6-30 months down to 2.5-9 months (Ette, Conscience, the law, and donation of expired drugs, Ann. Pharmacother. 38:1310-1313 (2004), which is herein incorporated by reference). As such, a medicinal storage container may be used in extreme tropical conditions, for example, to maintain a medication at a temperature consistent with an optimal shelf life.

Example 4

A medicinal storage container may be used, for example, to maintain a drug or drugs used for the treatment of HIV/AIDS at or below 25° C. For example, the combination of lopinavir and ritonavir, one of several anti-retroviral options recommended by the WHO for the treatment of HIV/AIDS in developing or resource-limited countries, is optimally stored at 2-8° C. until dispensing, after which it may be kept at 25° C. or less for approximately two months. However, sustained exposure of lopinavir/ritonavir to 35° C. for eight weeks, for example, results in a 10-20% loss in drug potency, while exposure to as little as 7 days at 45° C. results in a 40% reduction in potency and physical melting of the capsules (Pau et al., Instability of lopinavir/ritonavir capsules at ambient temperatures in sub-Saharan Africa: relevance to WHO antiretroviral guidelines, AIDS (2005) 19:1233-1234, which is herein incorporated by reference). As such, a single dose of an HIV/AIDS medication or medication combination may be enclosed in an integrally sealed medicinal storage container. Alternatively, multiple doses of an HIV/AIDS medication or medication combination may be enclosed in an integrally sealed medicinal storage container for use by multiple individuals on a given day, or for dosing one individual over a short time frame such as, for example, several days to a week. Multiple doses of an HIV/AIDS medication or medication combination may be optionally enclosed in a medicinal storage container and as such a single unit or multiple units may be dispensed over time without compromising the temperature of the remaining stored units.

Example 5

A medicinal storage container may also be used to maintain oral medications used for the treatment of malaria, for example, at an optimal temperature. For example, chloroquine in tablet form is commonly used for the treatment of malaria in developing countries, but loses as much as 50% of its bioavailability after 6 months of storage at 40° C. and 75% relative humidity (Risha et al., In vitro evaluation of the quality of essential drugs on the Tanzanian market, Trop. Med. Int. Health 7:701-707 (2002), which is herein incorporated by reference). Sulfadoxine and pyrimethamine, a common anti-malarial combination, may also experience decreased bioavailability after sustained exposure to the heat and humidity commonly encountered in tropical climates (Risha et al., In vitro evaluation of the quality of essential drugs on the Tanzanian market, Trop. Med. Int. Health 7:701-707 (2002), which is herein incorporated by reference). As such, a single dose of an anti-malarial medication or medication combination may be enclosed in an integrally sealed medicinal storage container. Alternatively, multiple doses of an anti-malarial medication or medication combination may be enclosed in an integrally sealed medicinal storage container for use by multiple individuals on a given day, or for dosing one individual over a short period of time such as, for example, a 3 to 5 day treatment course (see, e.g. Llanos-Cuentas et al., Atovaquone and proguanil hydrochloride compared with chloroquine or pyrimethamine/sulfadoxine for treatment of acute Plasmodium falciparum malaria in Peru, Braz. J. Infect. Dis. 5:67:72 (2001), which is herein incorporated by reference). Multiple doses of an anti-malarial medication or medication combination may be optionally enclosed in a medicinal storage container and as such a single unit or multiple units may be dispensed over time without compromising the temperature of the remaining units.

Example 6

A medicinal storage container may also be used to maintain oral medications such as, for example, oral solutions used for pediatric care at an optimal temperature. For example, an oral solution of stavudine is commonly used for treating young children with HIV/AIDS in developing countries, but loses 84% of its activity after 2 weeks of storage at 35° C. (Lockman et al., Stability of didanosine and stavudine pediatric oral solutions and Kaletra capsules at temperatures from 4° C. to 55° C. Conf. Retrovir. Opportunistic Infect. (2005) February 22-25; 12: abstract no. 668, which is herein incorporated by reference). In some instances, an oral solution might be a vaccine such as, for example, an oral polio vaccine or a rotavirus vaccine. As such, a single dose of an oral solution medication such as an HIV/AIDS medication or vaccine, for example, may be enclosed in an integrally thermally sealed medicinal storage container to maintain an optimal storage temperature, for example, of 2 to 8° C. In some instances, the optimal temperature may range from 2 to 25° C. The solution may be directly packaged in a medicinal storage container. Alternatively, the solution may be separately packaged in a tube, cup, vial, or other dosing unit. Optionally, multiple doses of an oral solution medication may be enclosed in an integrally sealed medicinal storage container, either with or without separate packaging, for use by multiple individuals on a given day, or for dosing one individual over a short time frame such as, for example, several days to a week. Multiple doses of an oral solution medication may be optionally enclosed in a medicinal storage container and as such a single unit or multiple units may be dispensed over time without compromising the temperature of the remaining units. Optionally, a single or multiple doses of an oral solution medication may be stored in medicinal storage container with an access region, as described herein.

Example 7

A medicinal storage container may be used to maintain prepackaged single use injectable medications at an optimal storage temperature. For example, a medicinal storage container may contain single doses of depot-medroxyprogesterone (DMPA-SC) (birth control), Hepatitis B vaccines, oxytocin (postpartum hemorrhage prevention), and gentamicin (sepsis prevention in neonates) prefilled, for example, in a Uniject syringe device (see, e.g. PATH, The Radically Simple Uniject™ Device; Levin et al., The costs of home delivery of a birth dose of hepatitis B vaccine in a prefilled syringe in Indonesia, Bull. World Health Org., 83:456-462 (2005); and Bang et al., Effect of home-based neonatal care and management of sepsis on neonatal mortality: field trial in rural India, Lancet, 354:1955-1961 (1999), which are each herein incorporated by reference). As such, one or more single-dose, prepackaged injectable medication devices may be stored at an optimal temperature in an integrally thermally sealed medicinal storage container. Optionally, one or more prepackaged injectable medication devices may be stored at an optimal temperature in a medicinal storage container with an inner assembly as described herein. Alternatively, a medicinal storage container may maintain cartridges, vials, or ampules at an optimal temperature for use with a needle-free injection device, for example. A medicinal storage container may include an operable attachment to a medicinal dispensing device, such as a needle-free injection device.

Example 8

A medicinal storage container may be used to maintain a diagnostic test kit or kits, for example, at an optimal storage temperature. A diagnostic kit might be a rapid diagnostic test, for example, such as those used to screen for malaria, HIV, hepatitis B, and syphilis in developing or resource-limited countries. These diagnostic kits are optimally stored in a temperature range of 2° C. to 30° C., but the anticipated shelf-life of any given kit is dependent upon maintaining the product within the optimal temperature range. This poses a challenge in remote or resource-limited parts of the world where temperatures may easily exceed 35° C. in summer months, with little or no available refrigeration. For example, investigators have found that malaria rapid diagnostic tests are routinely stored for extended periods of time above 30° C. in remote villages in Cambodia and the Philippines, diminishing the potential efficacy of the tests (Jorgensen et al., Malaria rapid diagnostic tests in tropical climates: The need for a cool chain, Am. J. Trop. Med. Hyg. (2006) 74:750-754, which is herein incorporated by reference). Similar issues regarding storage of malaria rapid diagnostic tests exist in remote and resource-limited areas in Africa (see, e.g., Moonasar et al., An exploratory study of factors that affect the performance and usage of rapid diagnostic tests for malaria in the Limpopo Province, South Africa, Malaria J. (2007) 6:74, which is herein incorporated by reference). As such, a medicinal storage container may be used to maintain a rapid diagnostic test in a temperature range of 2° C. to 30° C. from manufacture in or out of country to an end-user in a remote village, for example. A single rapid diagnostic test may be enclosed in an integrally thermally sealed medicinal storage container for testing a single individual, for example. Alternatively, multiple rapid diagnostic tests may be enclosed in an integrally thermally sealed medicinal storage container for testing multiple individuals on a given day or over a few days. Multiple rapid diagnostic tests may be optionally enclosed in a medicinal storage container with an inner assembly and as such a single unit or multiple units may be dispensed over time without compromising the temperature of the remaining units.

Example 9

In some instances, it may be appropriate to maintain a medical treatment at an elevated temperature. For example, a medicinal storage container may be used to maintain fluids intended for intravenous (IV) administration at or slightly above body temperature (generally 98.6° F./37° C.). In a medical or surgical setting, for example, a medicinal storage container may be used to hold artificial plasma or other blood product at appropriate temperature for immediate use. For example, plasma substitutes such as hydroxylethyl starch (HES) are often administered rapidly to patients with hypovolemia and for hemodilutional autotransfusion (HAT) during surgery and anesthesia (Yamakage et al. Safety and beneficial effect on body core temperature of prewarmed plasma substitute hydroxyethyl starch during anesthesia Anesthesiology (2004) 101:A1285, which is herein incorporated by reference). Addition of these agents at room temperature may result in a drop in the patient's core temperature and as such are best administered at or slightly above body temperature. HES has been shown to be stable at 40° C. for at least 3 months. As such, a blood product such as HES, for example, may be stored at 40° C. in an integrally thermally sealed medicinal storage container. The blood product may be packaged directly into the integrally thermally sealed medicinal storage container. Alternatively, the blood product may be packaged separately in an IV bag ranging in size, for example, from 50 to 1000 milliliters and stored in an integrally thermally sealed medicinal storage container. Optionally, multiple units of prepackaged blood product may be stored in a medicinal storage container with an inner assembly and as such a single unit or multiple units may be dispensed over time without compromising the temperature of the remaining stored units. In some instances, a blood product may be directly packaged in a medicinal storage container with an access region, as described herein.

Example 10

A medicinal storage container may also be used to maintain units of an intravenous (IV) fluid at or slightly above body temperature. For example, a medicinal storage container may hold one or more units of an IV fluid containing dextrose or saline for use, for example, in treating dehydration associated with hypothermia. As the core temperature of a hypothermic individual may already be below normal, administration of intravenous fluids should optimally be performed at body temperature to prevent further cooling (Department of Health & Social Services, State of Alaska, Cold Injuries Guidelines Revised version 2005, which is herein incorporated by reference). As such, a medicinal storage container may contain varying units of prewarmed rehydration fluid. For example, a medicinal storage container with an inner assembly including one or more interlocks and containing prewarmed rehydration solution may be used by first responders in the field such as, for example, a paramedic, an emergency medical technician, search and rescue, coast guard, or military personnel.

Example 11

A medicinal storage container with direct access under pressure may be used to maintain humidified air or oxygen in the range of 43-45° C. (107-122° F.), for example. In a hypothermic individual, loss of heat during respiration may account for 10% to 30% of the body's heat loss, particularly under conditions in which the ambient air temperature is cold. As such, inhalation of warm, water-saturated air is a noninvasive treatment suitable for active core rewarming in the field and donates heat directly to the head, neck, and thoracic core, warming the hypothalamus, the temperature regulation center, the respiratory center, and the cardiac center at the base of the brainstem. (Department of Health & Social Services, State of Alaska, Cold Injuries Guidelines Revised version 2005, which is herein incorporated by reference). In many cases, this rewarming of the central nervous system at the brainstem reverses the cold-induced depression of the respiratory centers and improves the level of consciousness. Alternatively, a medicinal storage container with an access region may contain water ranging in temperature, for example, from 99 to 212° F. (37-100° C.) that may be used in conjunction with a face mask to provide prewarmed, humidified air to a hypothermic individual. For example, inhaled ambient air may be passed over steaming, prewarmed water prior to entering an individual's lungs. As such, a temperature stabilized storage container with an access region may dispense a unit of prewarmed water to an external vessel attached to the breathing apparatus.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A temperature-stabilized medicinal storage container, comprising:
    a structural assembly including one or more sections of insulation material including at least one multilayer insulation material, the structural assembly primarily defining at least one substantially thermally sealed medicinal storage region configured to store medicinal units between approximately 2° Centigrade and approximately 8° Centigrade;
    an outlet assembly including one or more outlet channels, wherein the one or more outlet channels are arranged to provide controllable egress of a quantity of a stored material from the at least one substantially thermally sealed medicinal storage region, and the one or more outlet channels substantially follow a thermal pathway with a high aspect ratio;
    one or more heat sink units; and
    at least one selectively-operable thermal conduction unit between one or more of the at least one substantially thermally sealed medicinal storage region and at least one of the one or more heat sink units.

2. The temperature-stabilized medicinal storage container of claim 1, comprising:
    at least one layer of nontoxic material on an interior surface of one or more of the at least one substantially thermally sealed medicinal storage region.

3. The temperature-stabilized medicinal storage container of claim 1, comprising:
    at least one layer of material including at least one metal on an interior surface of one or more of the at least one substantially thermally sealed medicinal storage region.

4. The temperature-stabilized medicinal storage container of claim 1, wherein the one or more thermal variant units include:
    one or more active cooling units.

5. The temperature-stabilized medicinal storage container of claim 1, wherein the one or more thermal variant units include:
    one or more regions of thermal transfer within the container.

6. The temperature-stabilized medicinal storage container of claim 1, wherein one or more of the at least one selectively-operable thermal conduction unit includes:
    at least one thermally-conductive liquid fluid.

7. The temperature-stabilized medicinal storage container of claim 1, comprising:
    at least one controller operably coupled to one or more of the at least one selectively-operable thermal conduction unit; and
    at least one temperature sensor within the at least one substantially thermally sealed medicinal storage region.

8. The temperature-stabilized medicinal storage container of claim 1, comprising:
    one or more temperature sensors within the at least one substantially thermally sealed medicinal storage region.

9. The temperature-stabilized medicinal storage container of claim 1, comprising:
    at least one area within the container that is at a higher gaseous pressure than an atmospheric pressure external to the container.

10. The temperature-stabilized medicinal storage container of claim 1, wherein the at least one substantially thermally sealed medicinal storage region comprises:
    a plurality of substantially temperature-stabilized medicinal storage regions.

11. The temperature-stabilized medicinal storage container of claim 3, wherein the at least one layer of material including at least one metal comprises:
    silver.

12. The temperature-stabilized medicinal storage container of claim 1, wherein the one or more sections of the insulation material comprises:
    at least one layer of thermal reflective material: and
    at least one spacer unit adjacent to the at least one layer of thermal reflective material.

13. The temperature-stabilized medicinal storage container of claim 7, wherein one or more of the at least one controller comprises:
    an electronic controller.

14. The temperature-stabilized medicinal storage container of claim 7, wherein one or more of the at least one controller comprises:
    a mechanical controller.

15. The temperature-stabilized medicinal storage container of claim 1, comprising:
    one or more sensor of an identity of an item within one or more of the at least one storage region.

16. The temperature-stabilized medicinal storage container of claim 1, comprising:
    one or more communications devices.

17. The temperature-stabilized medicinal storage container of claim 1, wherein the temperature-stabilized medicinal storage container comprises:
    no active cooling units.

* * * * *